(12) United States Patent
Bar-El et al.

(10) Patent No.: US 11,642,470 B2
(45) Date of Patent: May 9, 2023

(54) ANTI-C5 ANTIBODY DISPENSING INJECTOR AND METHOD OF INJECTION

(71) Applicant: West Pharma. Services IL, Ltd., Ra'anana (IL)

(72) Inventors: Yossi Bar-El, Beit Arye (IL); Gil Yigal, Gan Yavne (IL); Reuven Y. Filman, Tel Mond (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 389 days.

(21) Appl. No.: 16/778,229

(22) Filed: Jan. 31, 2020

(65) Prior Publication Data
US 2020/0254185 A1 Aug. 13, 2020

Related U.S. Application Data

(60) Provisional application No. 62/803,998, filed on Feb. 11, 2019.

(51) Int. Cl.
| | |
|---|---|
| *A61M 5/315* | (2006.01) |
| *C07K 16/28* | (2006.01) |
| *C12N 9/24* | (2006.01) |
| *A61M 5/46* | (2006.01) |
| *A61M 5/32* | (2006.01) |

(52) U.S. Cl.
CPC .... *A61M 5/31585* (2013.01); *A61M 5/31535* (2013.01); *A61M 5/32* (2013.01); *A61M 5/46* (2013.01); *C07K 16/2896* (2013.01); *C12N 9/2402* (2013.01); *A61M 2005/3284* (2013.01); *C07K 2317/526* (2013.01)

(58) Field of Classification Search
CPC .......... A61M 5/31585; A61M 5/31535; A61M 5/32; A61M 5/46; C07K 16/2896; C12N 9/2402
USPC ........................................................ 604/208
See application file for complete search history.

(56) References Cited

U.S. PATENT DOCUMENTS

| | | | |
|---|---|---|---|
| 9,079,949 B1 * | 7/2015 | Andrien, Jr. | ............... A61P 3/06 |
| 10,149,943 B2 * | 12/2018 | Bar-El | ............... A61M 5/31511 |

(Continued)

FOREIGN PATENT DOCUMENTS

WO 2018222521 A1 12/2018

*Primary Examiner* — Phillip A Gray
(74) *Attorney, Agent, or Firm* — Blank Rome LLP

(57) ABSTRACT

An injector includes an injector housing, an activation button assembly movably mounted to the injector housing and operatively connected to the injection needle, and a cartridge door movably mounted to the injector housing between an open position and a closed position. A deflectable interference member engaging the rear end flange of the cartridge has a resting position configured to limit an insertion depth of a cartridge into an interior channel of the cartridge door to a sealed position, wherein the cartridge piercing needle does not fully penetrate a pierceable septum of the cartridge. The cartridge door includes an interior channel having a cartridge mounted therein. The cartridge includes a substance to be dispensed. The substance includes an anti-C5 antibody or antigen binding fragment thereof, and optionally further includes a recombinant human hyaluronidase enzyme. A method of treating a complement associated condition using an injector thereof. A method of dispensing a substance from an injector thereof.

26 Claims, 15 Drawing Sheets

Specification includes a Sequence Listing.

(56) References Cited

U.S. PATENT DOCUMENTS

2016/0346478 A1 12/2016 Bar-El et al.
2018/0154081 A1* 6/2018 Bar-El ................ A61M 5/2422

* cited by examiner

ANTI-C5 ANTIBODY DISPENSING INJECTOR AND METHOD OF INJECTION

CROSS-REFERENCE TO RELATED APPLICATIONS

The present application claims the benefit of priority to U.S. Provisional Application No. 62/803,998, filed Feb. 11, 2019, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688210-503U1", creation date of Jan. 15, 2020, and having a size of 12.0 KB. The sequence listing submitted via EFS-Web is part of the specification and is herein incorporated by reference in its entirety.

BACKGROUND OF THE DISCLOSURE

The present disclosure is generally directed to a cartridge loaded injector, and, more particularly, to a medicament containing cartridge loaded injector configured to maintain a cartridge loaded therein in a sealed state until the device is activated for use.

An injector, such as, for example, a drug injector, is typically loaded with a cartridge containing therein a medicament to be dispensed. The cartridge may be pre-loaded prior to delivery to a user/subject, or, alternatively, the cartridge may be loaded by the user prior to use. Generally, the cartridge is sealed prior to loading, i.e., insertion, into the injector and unsealed during loading into the injector to place the substance within the cartridge in fluid communication with an injection needle of the injector.

One drawback of such a sequence is that the loaded cartridge may be left in an unsealed state for an excessive period of time prior to device activation, i.e., injection of the substance into the user/subject. The unsealed cartridge is susceptible to leakage and/or contamination, rendering at least the cartridge unsuitable for use. Alternatively, the substance within the unsealed cartridge may flow into the fluid pathway connecting to the injection needle and dry or solidify prior to device activation, thereby potentially obstructing the fluid pathway and rendering the injector unusable. Moreover, once a cartridge is unsealed, it cannot be re-used. Therefore, if a user mistakenly loads the cartridge into the injector prematurely, or, if the injection is otherwise not performed, e.g., device malfunction, the unsealed cartridge is lost.

Therefore, it would be advantageous to manufacture an injector configured to maintain a cartridge loaded therein in a sealed state until the device is activated for use.

BRIEF SUMMARY OF THE INVENTION

According to an aspect of some embodiments of the invention, there is provided an injector that includes an injector housing; an injection needle translatable between a retracted position, wherein at least a tip of the injection needle is contained within the injector housing, and an injection position, wherein at least the tip of the injection needle protrudes from the injector housing; an activation button assembly movably mounted to the injector housing and operatively connected to the injection needle, the activation button assembly being translatable from an unactuated position to an actuated position to drive the injection needle from the retracted position thereof to the injection position thereof; a cartridge door movably mounted to the injector housing between an open position and a closed position, the cartridge door that includes: an open end, an interior channel having a cartridge mounted therein, the cartridge containing a substance to be dispensed and having an opening at a front end of the cartridge sealed by a pierceable septum and a flange at a rear end thereof, and a cartridge piercing needle mounted within the interior channel and connected in fluid communication with the injection needle, the cartridge piercing needle being configured to fully penetrate the pierceable septum of the cartridge to connect the substance within the cartridge in fluid communication with the injection needle; and a deflectable interference member engaging the rear end flange of the cartridge in a resting position of the interference member, thereby limiting an insertion depth of the cartridge into the interior channel of the cartridge door to a sealed position, wherein the cartridge piercing needle does not fully penetrate the pierceable septum; wherein: the cartridge door is movable to the closed position thereof in the sealed position of the cartridge, and movement of the activation button assembly from the unactuated position to the actuated position thereof, in the closed position of the cartridge door, deflects the interference element out of engagement with the rear end flange of the cartridge, thereby enabling further advancement of the cartridge into the interior channel of the cartridge door to an unsealed position, wherein the cartridge piercing needle fully penetrates the pierceable septum; and wherein the substance includes an anti-C5 antibody or antigen binding fragment thereof including heavy chain complementarity determining regions (CDRs) HCDR1, HCDR2, and HCDR3 of SEQ ID NOs: 1, 2, and 3, respectively; light chain CDRs LCDR1, LCDR2, and LCDR3 of SEQ ID NOs: 4, 5, and 6, respectively; and a variant human IgG Fc constant region that binds to human neonatal Fc receptor (FcRn), wherein the CH3 domain of the variant human Fc constant region includes Met-429-Leu and Asn-435-Ser substitutions at residues corresponding to methionine 428 and asparagine 434 of a native human IgG Fc constant region, each in EU numbering, and wherein the substance optionally further includes a recombinant human hyaluronidase enzyme.

According to some embodiments of the invention, the injector further includes a driving assembly engageable with the cartridge to expel the substance therefrom, the driving assembly being operatively engaged with the activation button assembly and being configured to drive the cartridge from the sealed position to the unsealed position upon movement of the activation button assembly from the unactuated position to the actuated position.

According to some embodiments of the invention, the deflectable interference member includes a cantilevered arm.

According to some embodiments of the invention, the cantilevered arm defines a first end connected to the cartridge door and extends to a second, free end proximate the open end of the cartridge door.

According to some embodiments of the invention, the cartridge door includes a sidewall and the cantilevered arm defines a deflectable portion of the cartridge door sidewall.

According to some embodiments of the invention, the sidewall of the cartridge door defines a first internal perimeter at the second, free end of the cantilevered arm when the cantilevered arm is in the resting position thereof, and the sidewall of the cartridge door defines a second internal perimeter at the second, free end of the cantilevered arm when the cantilevered arm is deflected from the resting position thereof, the first internal perimeter being smaller than a largest outer perimeter of the cartridge insertable into the interior channel, thereby limiting the insertion depth of the cartridge into the interior channel of the cartridge door, and the second internal perimeter being greater than the largest outer perimeter of the cartridge, thereby enabling further advancement of the cartridge into the interior channel of the cartridge door.

According to some embodiments of the invention, the activation button assembly includes a post extending therefrom to a terminal end having a tapered face, the post having a post pathway along which the post travels from the unactuated position of the activation button assembly to the actuated position of the activation button assembly, and wherein the cantilevered arm includes a tab laterally extending therefrom toward the post pathway, the tab having a hooked end facing the tapered face of the post, wherein movement of the activation button assembly from the unactuated position to the actuated position, in the closed position of the cartridge door, engages the post with the tab, the tapered face engaging and laterally translating the hooked end, and, in turn, deflecting the cantilevered arm away from the resting position thereof.

According to some embodiments of the invention, the injector further includes a biasing member connected with the activation button assembly and the injection needle, the biasing member being stabilized in a stored energy state in the unactuated position of the activation button assembly, and released in the actuated position of the activation button assembly into an energy releasing state to drive the injection needle from the retracted position thereof to the injection position thereof, wherein: a position of the activation button assembly between the unactuated position thereof and the actuated position thereof defines a threshold point, and movement of the activation button assembly beyond the threshold point secures the activation button assembly in the actuated position and the injection needle in the injection position.

According to some embodiments of the invention, the biasing member biases the activation button assembly into the unactuated position thereof and returns the activation button assembly to the unactuated position thereof in response to movement of the activation button assembly not surpassing the threshold point.

According to some embodiments of the invention, the injector further includes a needle hub movably mounted within the injector housing, the injection needle being supported by the movable needle hub and the needle hub and the injection needle being translatable between the retracted position and the injection position.

According to some embodiments of the invention, the injector further includes an elongate first post connected with the injector housing and projecting upwardly therefrom, the elongate first post having an upper end including a downwardly inclined surface and an undercut underlying the inclined surface; a deflectable second post connected with the injector housing and projecting upwardly therefrom, the deflectable second post including a flange supporting a portion of the needle hub thereon, thereby securing the needle hub and the injection needle in the retracted position thereof; and the activation button assembly includes a downwardly projecting first arm having a flanged terminal end slidable along the inclined surface of the elongate first post, the first arm being elastically deflectable from an original state thereof; wherein: movement of the activation button assembly slides the flanged terminal end of the first arm along the inclined surface of the first post, thereby elastically deflecting the first arm away from the original state thereof; the inclined surface and the undercut of the elongate first post meet at a vertex defining the threshold point, and movement of the activation button assembly beyond the vertex triggers retraction of the first arm back toward the original state thereof, hooking the flanged terminal end thereof onto the undercut of the elongate first post and securing the activation button assembly in the actuated position thereof, and movement of the activation button beyond the vertex also engages the flanged terminal end of the first arm with the second post and deflects the second post, whereby the deflected second post releases the needle hub, and, in turn, releases the biasing member into the energy releasing state to drive the needle hub and the injection needle from the retracted position thereof to the injection position thereof.

According to an aspect of some embodiments of the present invention, there is provided a method of treating a complement associated condition selected from the group consisting of atypical hemolytic uremic syndrome (aHUS) and/or paroxysmal nocturnal hemoglobinuria (PNH) in a subject in need thereof. In one embodiment, the method includes delivering an anti-C5 antibody, or antigen binding fragment thereof, to a tissue site within the subject using an injector of the present invention.

According to an aspect of some embodiments of the present invention, there is provided a method of dispensing a substance from an injector, the injector having an injector housing, an injection needle movable from a retracted position, wherein at least a tip of the injection needle is contained within the injector housing, and an injection position, wherein at least the tip of the injection needle protrudes from the injector housing, an activation button assembly movably mounted to the injector housing and operatively connected to the injection needle, a cartridge door movably mounted to the injector housing between an open position and a closed position, the cartridge door having an open end, an interior channel, and a cartridge piercing needle mounted within the interior channel and connected in fluid communication with the injection needle, and a driving assembly operatively engaged with the activation button assembly and engageable with the cartridge. In one embodiment, the method includes inserting a cartridge into the interior channel of the cartridge door in the open position of the cartridge door, the cartridge containing the substance in a sealed reservoir thereof and having an opening at a front end of the reservoir sealed by a pierceable septum and a flange at a rear end of the reservoir, engaging the rear end flange of the cartridge with a deflectable interference member of the injector in a resting position of the interference member, thereby limiting an insertion depth of the cartridge into the interior channel of the cartridge door to a sealed position, wherein the cartridge piercing needle does not fully penetrate the pierceable septum; moving the cartridge door into the closed position thereof; moving the activation button assembly from an unactuated position to an actuated position thereof, and, in turn: deflecting the interference member out of engagement with the rear end flange of the cartridge, activating the driving assembly to advance the rear end flange of the cartridge past the interference member and drive the cartridge from the sealed position to an unsealed position, wherein the cartridge piercing needle fully penetrates the pierceable septum of the cartridge and connects the substance within the cartridge in fluid communication with the injection needle, and driving the injection needle from the retracted position to the injection position and dispensing the substance therefrom; wherein the substance comprises an anti-C5 antibody or antigen binding fragment thereof comprising heavy chain complementarity determining regions (CDRs) HCDR1, HCDR2, and HCDR3 of SEQ ID NOs: 1, 2, and 3, respectively; light chain CDRs LCDR1, LCDR2, and LCDR3 of SEQ ID NOs: 4, 5, and 6, respectively; and a variant human IgG Fc constant region that binds to human neonatal Fc receptor (FcRn), wherein the CH3 domain of the variant human Fc constant region comprises Met-429-Leu and Asn-435-Ser substitutions at residues corresponding to methionine 428 and asparagine 434 of a native human IgG Fc constant region, each in EU numbering, and wherein the substance optionally further comprises a recombinant human hyaluronidase enzyme.

According to some embodiments of the invention, the method further includes the step of placing the injector on a skin surface of a subject, and wherein the driving of the injection needle to the injection position comprises protruding at least the tip of the injection needle from the injector housing, through the skin surface of the subject and into an underlying tissue site, and dispensing the substance from the injection needle and into the tissue site.

According to some embodiments of the invention, the injector further includes a sensor connected to a control assembly, the method further includes detecting, via the sensor, at least one of (i) movement of the activation button assembly from the unactuated position thereof to the actuated position thereof and (ii) movement of the injection needle from the retracted position thereof into the injection position thereof; and activating the driving assembly, via the control assembly, upon said detecting.

According to some embodiments of the invention, the activation button assembly includes a post extending therefrom to a terminal end having a tapered face, the post having a post pathway along which the post travels from the unactuated position of the activation button assembly to the actuated position of the activation button assembly, and wherein the interference member includes a cantilevered arm defining a deflectable portion of a sidewall of the cartridge door, whereby a first end of the cantilevered arm is connected to the sidewall and extends to a second, free end proximate the open end of the cartridge door, the cantilevered arm including a tab laterally extending therefrom toward the post pathway, the tab having a hooked end facing the tapered face of the post, and wherein the moving of the activation button assembly from the unactuated position to the actuated position thereof comprises engaging the tapered face of the post with the hooked end of the tab, laterally translating the hooked end, and, in turn, deflecting the cantilevered arm out of engagement with the rear end flange of the cartridge.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Figure 1:
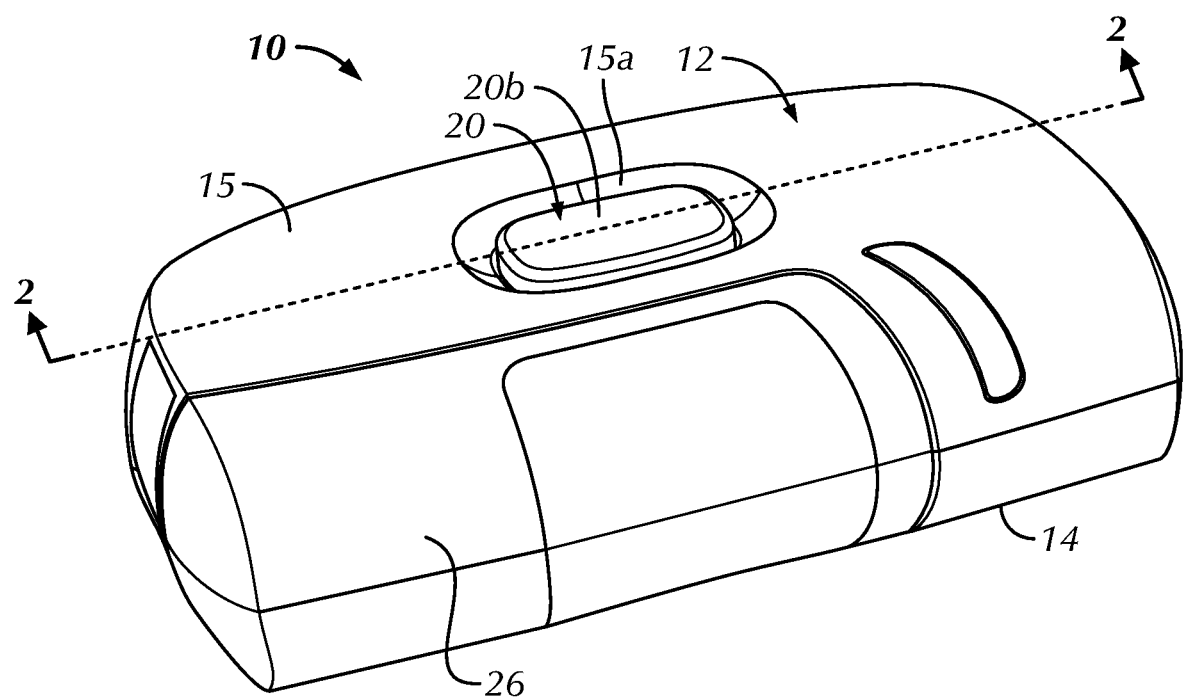
FIG. 1 is a top and front perspective view of a wearable injector, in accordance with an embodiment of the present disclosure.
Figure 2:
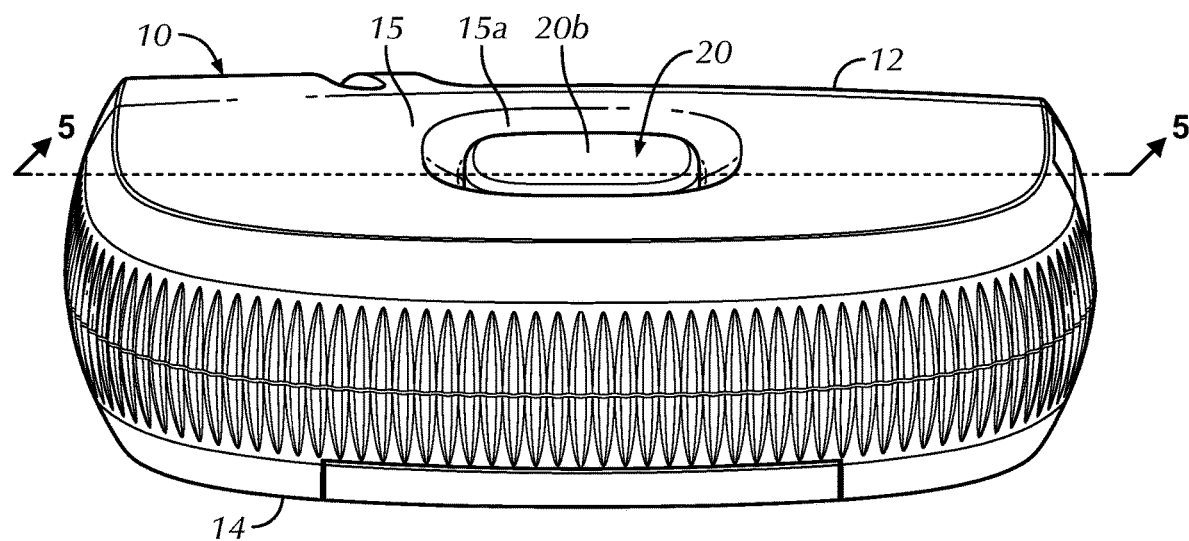
FIG. 2 is a top and rear perspective view of the injector of FIG. 1.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-13 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. As should be understood by those of ordinary skill in the art, the injector 10 generally includes a housing 12 having a first surface 14 configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface 15 opposing the first surface 14. In the illustrated embodiment, the second surface 15 defines a top, external surface of the injector housing 12, but the disclosure is not so limited.

Figure 3:
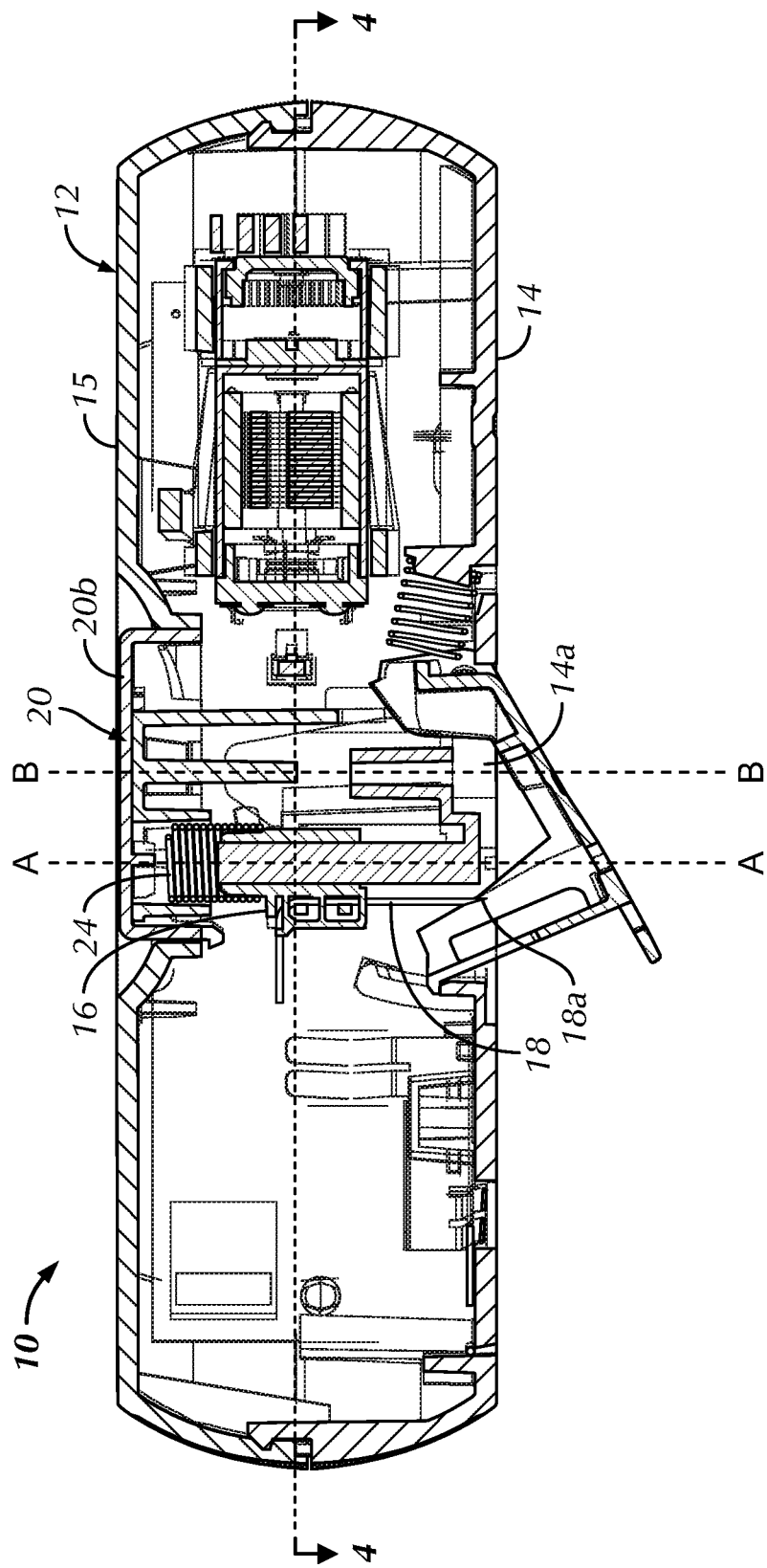
FIG. 3 is a cross-sectional view of the injector of FIG. 1, taken along the sectional line 2-2 of FIG. 1, with an activation button assembly in an unactuated position thereof and an injection needle in a retracted position thereof.
Figure 4:
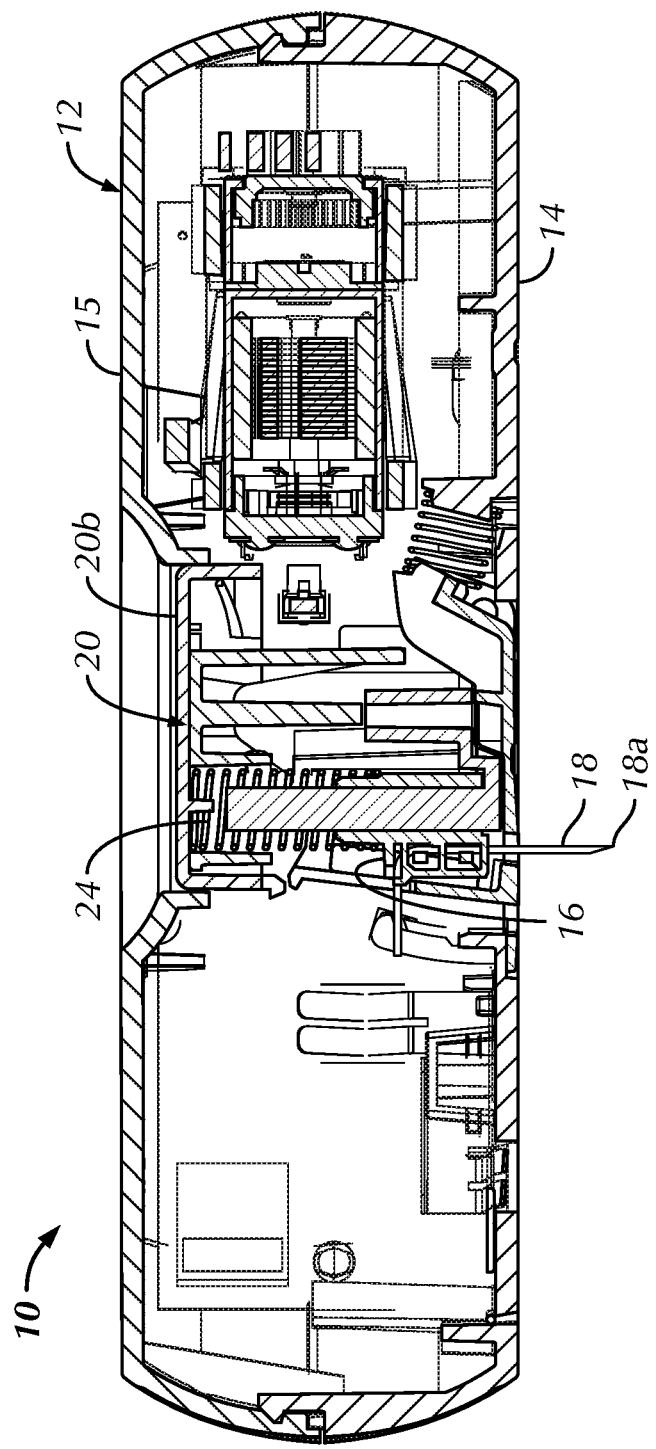
FIG. 4 is a cross-sectional view of the injector of FIG. 1, taken along the sectional line 2-2 of FIG. 1, with the activation button assembly in an actuated position thereof and the injection needle in an injection position thereof.

As shown in FIGS. 3-4, a needle hub 16, constructed, for example, from a polymeric or metal material, combinations thereof, or the like, is movably mounted within the injector housing 12 and an injection needle 18 is supported by the movable needle hub 16 in a manner well understood by those of ordinary skill in the art. In the illustrated embodiment, the needle hub 16 and the injection needle 18 are axially translatable (or otherwise displaceable) in the direction of axis A (FIG. 3) extending substantially perpendicularly to the first surface 14, between a retracted position (FIG. 3), wherein at least a tip 18a of the injection needle 18 is contained within the injector housing 12, and an injection position (FIG. 4), wherein at least the tip 18a of the injection needle 18 protrudes from the injector housing 12 through the opening 14a. As should be understood by those of ordinary skill in the art, however, the axis A may be positioned at angles other than 90° relative to the first surface 14. As also should be understood, the injection needle 18 may be movably mounted within the injector housing 12 via other mechanisms than the needle hub 16.

A depressible activation button assembly 20, constructed, for example, from a polymeric or metal material, a combination thereof, or the like, is movably mounted to the injector housing 12 and operatively connected to the injection needle 18 (as will be described in further detail). In the illustrated embodiment, the activation button assembly 20 is positioned within a cradle indent 15a in the second surface 15 of the injector housing 12, but the disclosure is not so limited. The cradle indent 15a defines an opening in the second surface 15, through which the activation button assembly 20 extends into the interior of the injector housing 12. The activation button assembly 20 is translatable along a button axis B, parallel to the axis A, from an unactuated position (FIGS. 1-3, 5) to an actuated position (FIGS. 4, 8) (as will be described in further detail below). In the illustrated embodiment, the injector housing 12 includes a securing post 12a (shown best in FIGS. 6, 8) projecting upwardly from the first surface 14 toward the second surface 15 along the button axis B. The securing post 12a slidably receives a complementary translation post 20a (shown best in FIGS. 6, 8) projecting downwardly from the activation button assembly 20 along the button axis B. The translation post 20a is configured, i.e., shaped and dimensioned, to matingly slide within the securing post 12a during translation of the activation button assembly 20 with respect to the injector housing 12 to assist in stabilizing translation of the activation button assembly 20 along the button axis B.

As shown in FIGS. 5-8, a biasing member 22 is operatively connected with the activation button assembly 20 and the injection needle 18. The biasing member 22 is stabilized in a stored energy state in the unactuated position of the activation button assembly 20 (FIG. 5) and released in the actuated position (FIG. 8) of the activation button assembly 20 into an energy releasing state to drive the injection needle 18 along the direction of axis A from the retracted position thereof to the injection position thereof. As should be understood by those of ordinary skill in the art, the stored energy state of the biasing member 22 is a state in which the biasing member 22 stores at least some potential energy. The energy releasing state of the biasing member 22 is a state of the biasing member 22 in which the biasing member 22 releases at least some of the stored potential energy from the stored energy state.

In the illustrated embodiment, the biasing member 22 takes the form of a coil spring expandable from the energy storing state, in which the spring 22 is at least partially compressed, to the energy releasing state, in which the spring 22 is expanded relative to the energy storing state. As should be understood by those of ordinary skill in the art, however, the biasing member 22 may alternatively take the form of other members capable of storing and releasing energy. Non-limiting examples include other springs (e.g., torsion or leaf springs), elastic bands, pneumatic pistons and the like. Alternatively, the biasing member 22 may take the form of an actuator configured to apply a translational force onto the injection needle 18.

In the illustrated embodiment, the coil spring 22 is mounted between the needle hub 16 and the activation button assembly 20, i.e., the spring 22 abuts the activation button assembly 20 at one end and abuts the needle hub 16 at an opposing end. In the energy storing state thereof, the spring 22 applies a biasing force at the one end on the activation button assembly 20, biasing the activation button assembly 20 into the unactuated position thereof, and also applies an oppositely directed biasing force at the other end on the needle hub 16.

Figure 5:
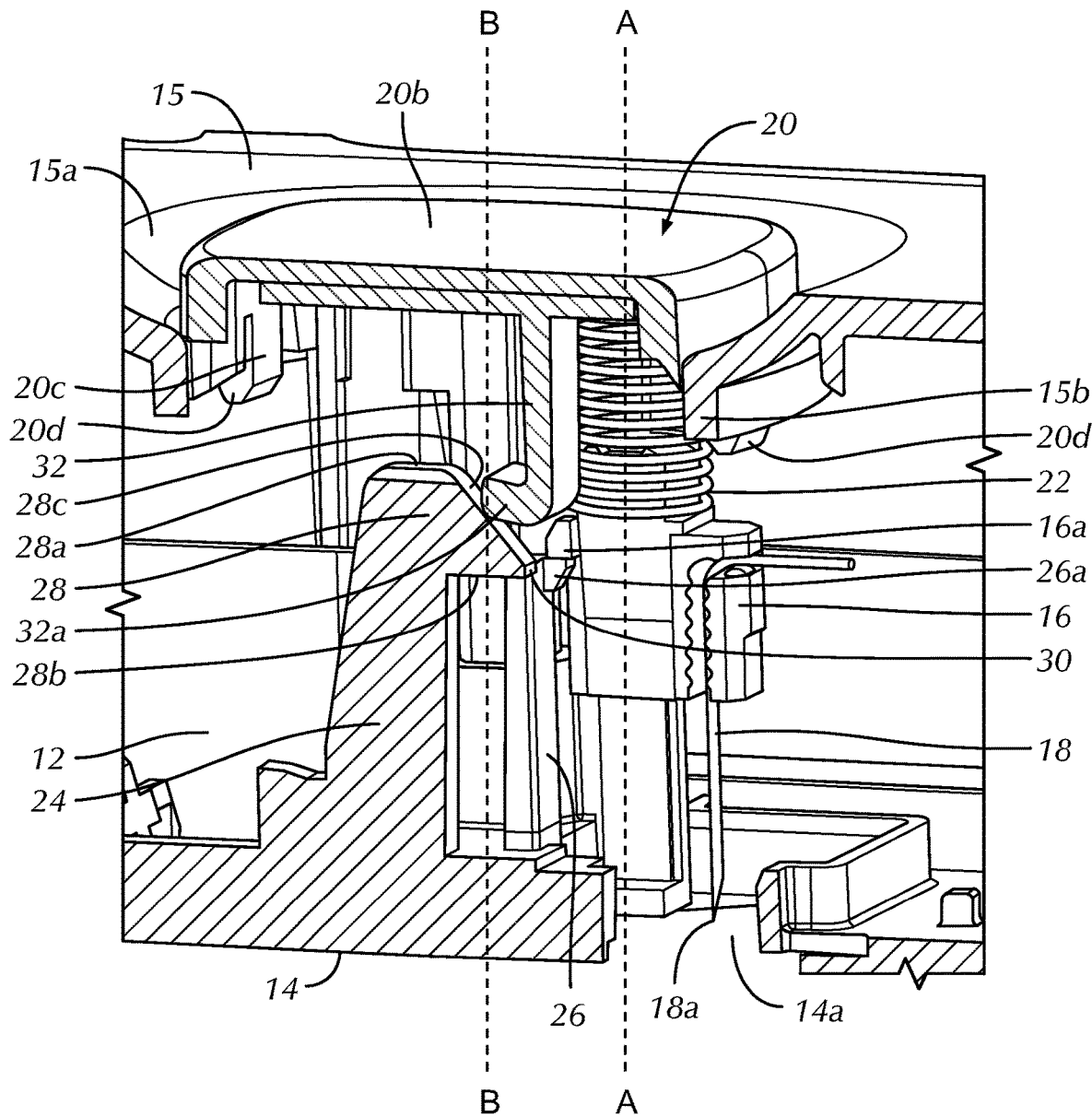
FIG. 5 is an enlarged partial cross-sectional view of an activation button assembly and an injection needle insertion mechanism of the injector of FIG. 1, taken along the sectional line 5-5 of FIG. 2, with the activation button assembly in an unactuated position thereof and the injection needle in a retracted position thereof.
Figure 6:
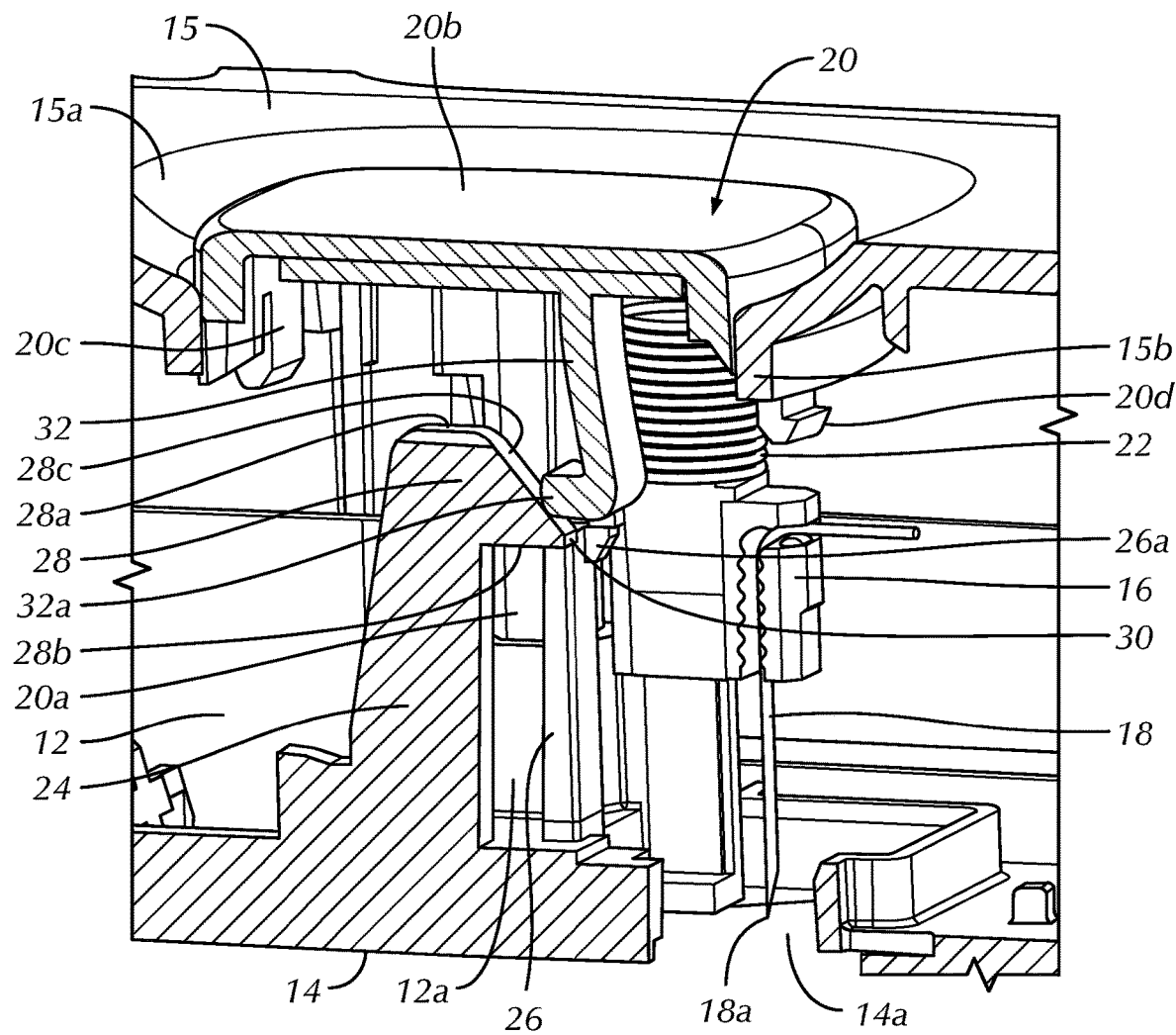
FIG. 6 is an enlarged partial cross-sectional view of the activation button assembly and the injection needle insertion mechanism of the injector of FIG. 1, taken along the sectional line 5-5 of FIG. 2, with the activation button assembly moved toward an actuated position thereof and the injection needle in the retracted position thereof.
Figure 7:
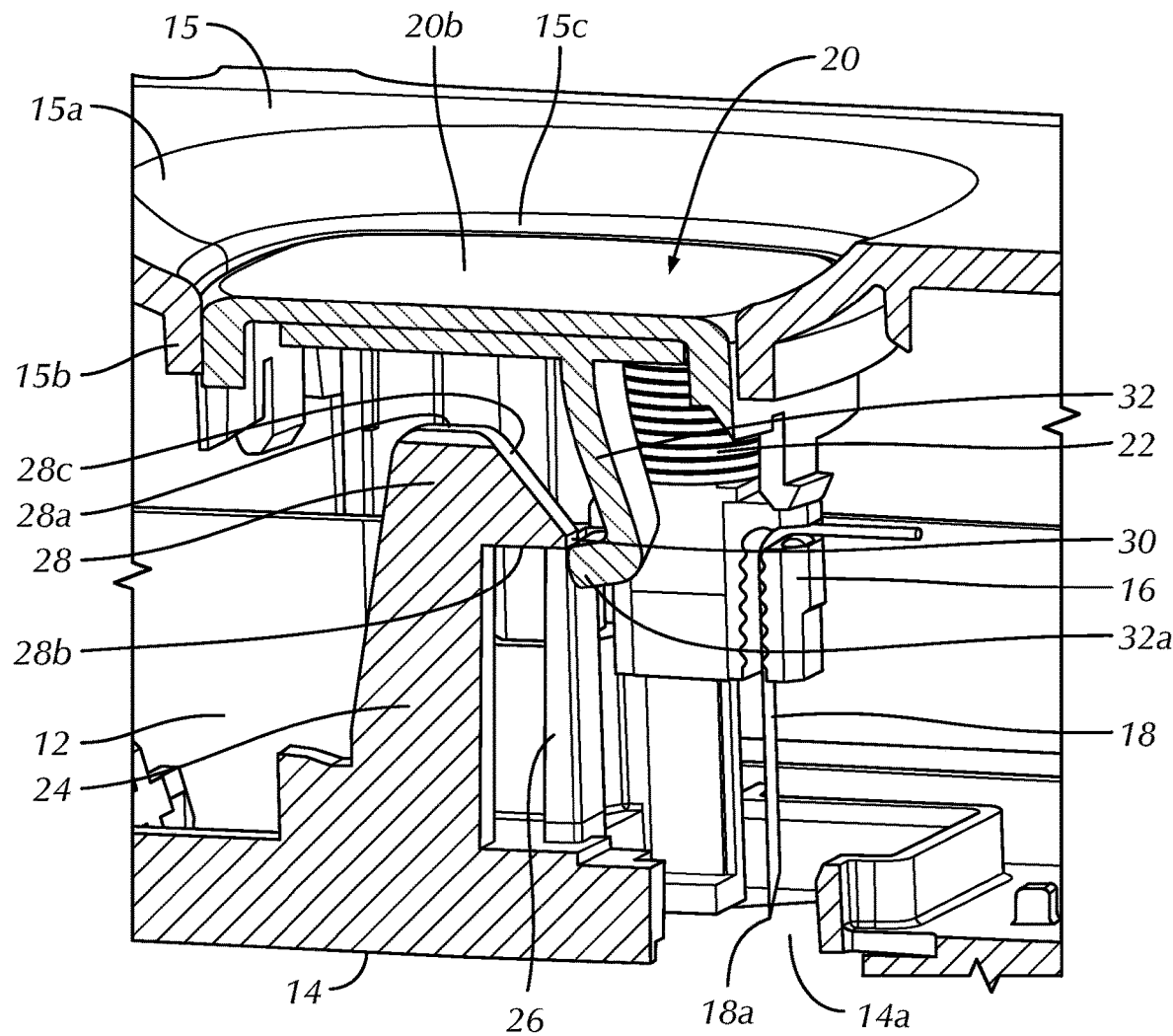
FIG. 7 is an enlarged partial cross-sectional view of the activation button assembly and the injection needle insertion mechanism of the injector of FIG. 1, taken along the sectional line 5-5 of FIG. 2, with the activation button assembly further moved toward the actuated position thereof and the injection needle in the retracted position thereof.

As shown best in FIG. 5, the activation button assembly 20 defines an external surface 20b, e.g., the top surface of the button assembly 20 engageable by a user, and a plurality of angularly spaced members 20c extending therefrom and forming respective hook shaped terminal ends 20d. The members 20c may be integral, i.e., unitary and monolithic, with the surface 20b, but the disclosure is not so limited. The cradle indent 15a, within which the activation button assembly 20 is positioned, includes a flanged member 15b extending downwardly therefrom. In the unactuated position of the activation button assembly 20 (FIG. 5), the hook shaped terminal ends 20d of the members 20c engage the flanged member 15b under the biasing force of the spring 22, thereby maintaining the activation button assembly 20 in the unactuated position and preventing the activation button assembly 20 from being removed from the housing 12. As should be understood by those of ordinary skill in the art, however, the activation button assembly 20 may be secured in the unactuated position thereof via other means, currently known or that later become known. In the unactuated position, the external surface 20b of the activation button assembly 20 is substantially flush with the second surface 15 of the injector housing 12 (FIG. 5). As will be described in further detail below, the activation button assembly 20 is depressed within the cradle indent 15a in the actuated position relative to the unactuated position (FIG. 8), e.g., the external surface 20b is below the second surface 15a. As also should be understood, however, the activation button assembly 20 may alternatively be positioned differently relative to the injector housing 12 in the actuated and unactuated positions thereof, wherein the actuated position of the activation button assembly 20 remains visually different than the unactuated position thereof. For example, the activation button assembly 20 may be elevated relative to the second surface 15 in the unactuated position thereof. Advantageously, the visual and haptic differentiation between the activation button assembly 20 positions serves as an intuitive, noticeable and continuous indication for the user that the injector has been successfully activated and remains activated.

The opposite end of the spring 22, as indicated previously, abuts the needle hub 16 and applies a biasing force onto the needle hub 16 directed toward the first surface 14, along the direction of the axis A. The spring 22 is prevented from driving the needle hub 16 and the injection needle 18 into the injection position, however, until the activation button assembly 20 is moved into the actuated position, as will be described further below.

In the illustrated embodiment, as shown in FIGS. 5-8, the injector 10 includes an elongate first post 24 connected with the injector housing 12 and projecting upwardly therefrom, and a deflectable, second post 26 connected with the injector housing 12 and projecting upwardly therefrom. The first and second posts 24, 26 may be integral, i.e., unitary and monolithic, with the injector housing 12, but the disclosure is not so limited. The first and second posts 24, 26 may also each be constructed from a polymeric or metal material, combinations thereof, or the like. In the illustrated embodiment, the first and second posts, 24, 26 project upwardly from the first surface 14, but the disclosure is also not so limited, and the first and second posts 24, 26 may project from other portions of the injector housing 12. As shown best in FIGS. 5-6, the second post 26 includes a flange 26a projecting laterally therefrom. In the illustrated embodiment, the flange 26a projects laterally from a terminal, upper end of the second post 26, but the disclosure is not so limited. As should be understood, the flange 26a may project laterally from other portions of the second post 26, provided that the flange 26a is capable of performing the functions described herein. The flange 26a supports a portion of the needle hub 16 thereon, thereby securing the needle hub 16 and the injection needle 18 in the retracted position thereof, i.e., obstructing the spring 22 from driving the needle hub 16 and the injection needle 18 into the injection position. In the illustrated embodiment, the needle hub 16 includes a complementary laterally extending flange 16a abutting the flange 26a, but the disclosure is not so limited. As should be understood, however, others portions of the needle hub 16 may engage the flange 26a, such as, for example, without limitation, an underside of the needle hub 16. Accordingly, engagement of the hook shaped terminal ends 20d of the members 20c with the flanged member 15b of the cradle indent 15a at one end of the spring 22, and engagement of the flange 26a of the second post 26 with the flange 16a of the needle hub 16 at the opposing end of the spring 22, maintains the spring 22 in an energy storing state prior to movement of the activation button assembly 20 into the actuated position thereof (see FIG. 5).

The elongate first post 24 includes a terminal upper end defining a flange 28. The flange 28 includes an upper surface 28a, defining the upper end of the first post 24, a lower surface 28b projecting laterally from the first post 24 further than a lateral extent of the upper surface 28a, and a downwardly inclined surface 28c from the upper surface 28a to the lower surface 28b. The lateral projection of the lower surface 28b from the elongate post 24 defines an undercut underlying the inclined surface 28c. The inclined surface 28c and lower surface 28b, i.e., the undercut, of the elongate first post 24 meet at a vertex 30. The vertex 30 may take the form of a line edge, a curved edge, a chamfered edge as shown in the figures.

The activation button assembly 20 includes a first arm 32 projecting downwardly from the top surface 20b. The first arm 32 may be integral, i.e., unitary and monolithic, with the top surface 20b, but the disclosure is not so limited. Alternatively, for example, the first arm 32 may be attached to the activation button assembly 20 via other attachment means currently known or that later become known. The first arm 32 may also be constructed from a polymeric or metal material, combinations thereof, or the like. The first arm 32 includes a laterally projecting, flanged, terminal, lower end 32a, forming a generally hook-shaped end 32a of the first arm 32. The flange 32a is positioned facing the downwardly inclined surface 28c of the first post 24 in the unactuated position of the activation button assembly 20. In one embodiment, a lateral tip of the flange 32a may define a complementary incline to the inclined surface 28c for smoother sliding thereon. As should be understood by those of ordinary skill in the art, the position of the flange 28 along the first post 24 and the position of the flange 32a along the first arm 32 is not limited to the respective upper and lower ends of the first post 24 and the first arm 32, but rather may be moved so long as the flange 32a is positioned facing the downwardly inclined surface 28c.

The first arm 32 is constructed to be more elastically flexible than the elongate first post 24, and the second post 26 is constructed to be more elastically flexible than the first arm 32. That is, the first post 24 is constructed to define a greater bending stiffness, i.e., resistance against bending deformation, than the first arm 32, and the first arm 32 is constructed to define a greater bending stiffness than the second post 26. Such properties may be achieved via relative material properties, between the first post 24, the first arm 32 and the second post 26, relative dimensions between the first post 24, the first arm 32 and the second post 26, or a combination thereof.

As shown in FIGS. 5-8, depression of the activation button assembly 20 along the button axis B slides the flange 32a of the first arm 32 down the inclined surface 28c of the first post 24. As the first arm 32 is more elastically flexible, i.e., deflectable, than the first post 24, sliding of the flange 32a along the inclined surface 28c elastically deflects the first arm 32 (FIGS. 6, 7) from an original state, e.g., undeflected or less deflected, thereof (FIG. 5).

The vertex 30 defines a threshold point along the activation button assembly 20 pathway, and solely movement of the activation button assembly 20 beyond the vertex 30 secures the activation button assembly in the actuated position thereof. That is, movement of the first arm 32 of the activation button assembly 20 beyond the vertex 30 (FIG. 8) triggers retraction of the deflected first arm 32 back toward the original state thereof, and the flanged terminal end 32a thereof engages with the undercut 28b of the elongate first post 24, e.g., hooks or snaps back into engagement with the undercut 28b, to secure the activation button assembly in the actuated position thereof. Movement of the activation button assembly 20 that does not position the flange 32a beyond the vertex 30 (e.g., FIG. 6) results in return of the activation button assembly 20 to the unactuated position thereof. That is, depression of the activation button assembly 20 further compresses the spring 22 in the energy storing state thereof, thereby charging the spring 22 with additional potential energy, until the flange 32a extends beyond the vertex 30. Accordingly, movement of the activation button assembly 20 that does not extend the flange 32a beyond the vertex 30 results in the spring 22 driving the activation button assembly 20 back toward the unactuated position. Additionally, or alternatively, the elasticity of the deflected first arm 32 drives the first arm 32 back up the inclined surface 28c to return to original state thereof, thereby returning the activation button assembly 20 to the unactuated position thereof.

Figure 8:
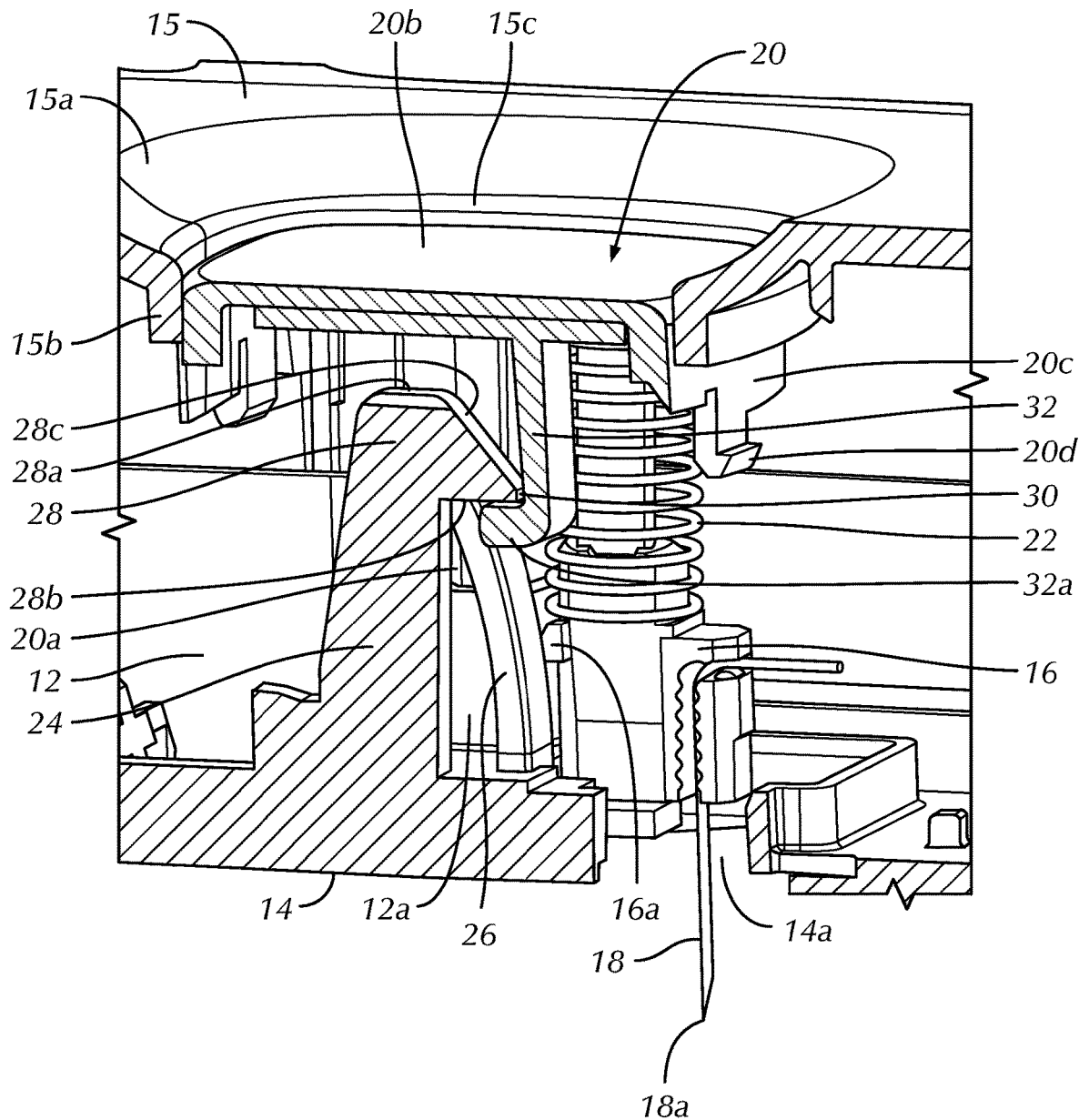
FIG. 8 is an enlarged partial cross-sectional view of the activation button assembly and the injection needle insertion mechanism of the injector of FIG. 1, taken along the sectional line 5-5 of FIG. 2, with the activation button assembly in the actuated position thereof and the injection needle in an injection position thereof.
Figure 9:
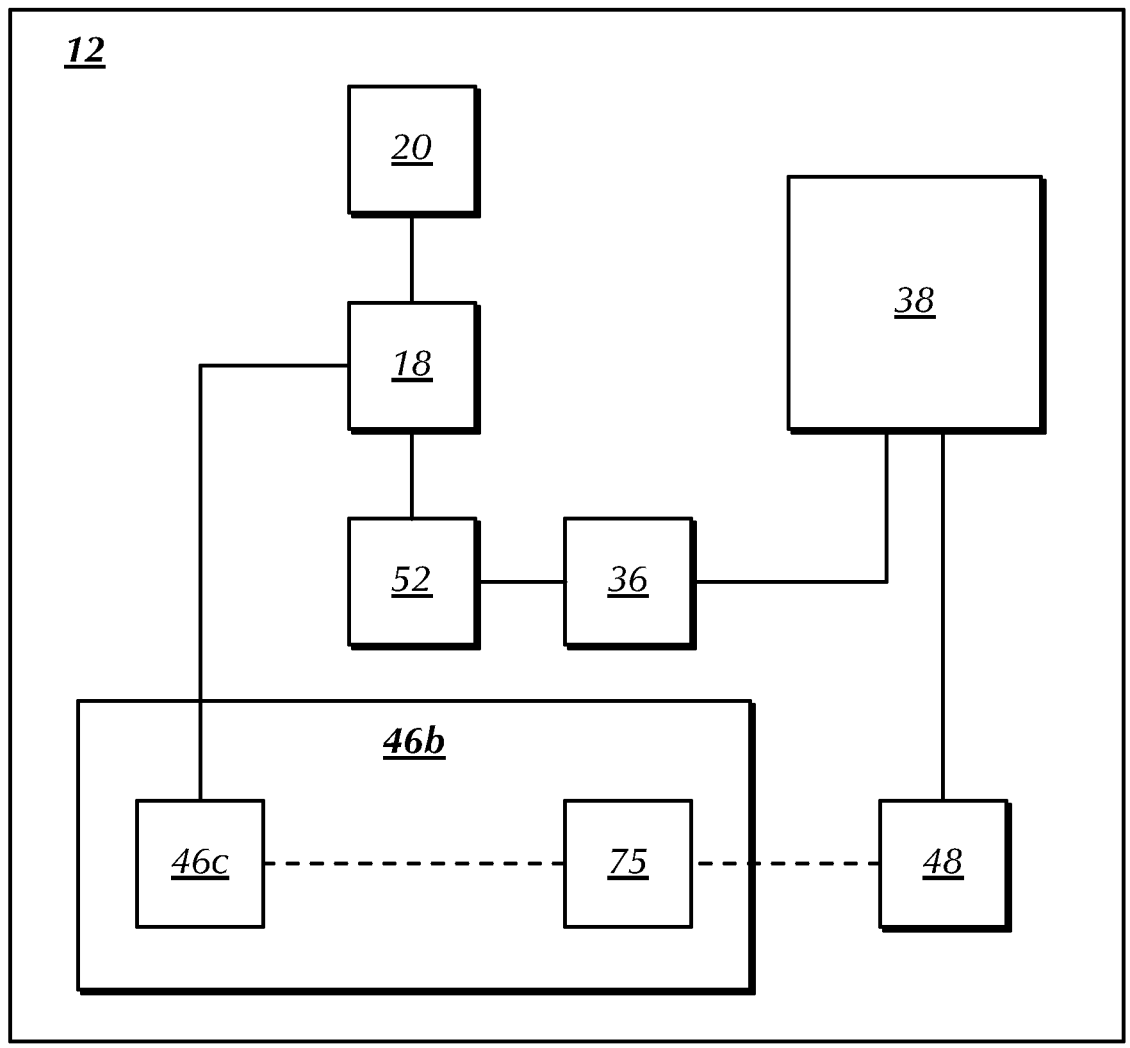
FIG. 9 is a schematic illustration of the operative connection between different components of the injector of FIG. 1, wherein the dotted lines illustrate an operative connection initiated upon injector activation.

Movement of the flange 32a of the first arm 32 beyond the vertex 30 of the first post 24, thereby triggering retraction of the deflected first arm 32 back toward the original, e.g., undeflected or less deflected, state thereof allows the flange 32a of the first arm 32 to engage with and deflect the second post 26 (due to the previously disclosed relative properties thereof) in the opposite direction. That is, the second post 26 is positioned such that return of the first arm 32 toward the original state thereof allows the first arm 32 to contact and deflect the second post 26. Accordingly, deflection of the second post 26 moves the flange 26a of the deflected second post 26 away from the flange 16a of the needle hub 16, thereby releasing the needle hub 16, and, in turn, releasing the spring 22 into the energy releasing state to drive the needle hub 16 and the injection needle 18 from the retracted position thereof to the injection position thereof (FIG. 8).

Thus, release of the spring 22 into the energy releasing state thereof is triggered upon movement of the first arm 32 of the activation button assembly 20 beyond the vertex 30, i.e., the threshold point/position.

Advantageously, therefore, insufficient user depression of the activation button assembly 20 that does not move the first arm 32 of the activation button assembly 20 into the original unused state thereof, without any negative affect on injection needle 18 deployment. Further advantageously, once the first arm 32 moves beyond the threshold point, the injection needle 18 is driven into the injection position thereof under the biasing force of the biasing member 22, irrespective of the force utilized to depress the activation button assembly 20. Thus, a desired preset injection force of the injection needle 18 may be configured during injector manufacture, according to the biasing force of the biasing member 22.

Turning primarily to FIGS. 9-13, the injector 10 further includes a cartridge door 46 defining an open end 46a for receiving, e.g., slidably, a cartridge 75 (FIGS. 10-13) therethrough, and an interior channel 46b to receive the cartridge 75 therein. The interior channel 46b may be sized and shaped to receive and stabilize the cartridge 75 therein. Alternatively, the interior channel 46b may include a cartridge cradle, a cartridge track, individual stabilizing members, combinations thereof, or the like (not shown) to receive and stabilize the cartridge 75 in the interior channel 46b.

As should be understood, the cartridge 75 includes a reservoir 75a having a first opening 75b and a second opening 75c. The reservoir 75a contains a substance (not shown), e.g., medicament, to be dispensed from the injector 10 through the injection needle 18. In the illustrated embodiment the first opening 75b of the cartridge 75 is a distal opening, but the location thereof is not so limited. The first opening 75b is sealed by a pierceable septum 77 in a manner well understood by those of ordinary skill in the art. In the illustrated embodiment the second opening 75c of the cartridge 75 is a proximal opening, but the location thereof is also not so limited. The second opening 75c is sealed by a piston 73 movably mounted within the reservoir 75a and sealingly engaged with an interior sidewall of the reservoir 75a in a manner well understood by those of ordinary skill in the art. The substance within the reservoir 75a is sealed between the piston 73 and the septum 77.

The second opening 75c of the cartridge 75 includes a flange 75d laterally extending therefrom. In the illustrated embodiment, the flange 75d is an annular flange, i.e., laterally extending from the entire perimeter of the second opening 75c, but the disclosure is not so limited. As should be understood, the flange 75d may extend from only a portion of the perimeter (less than the entirety thereof) of the second opening 75c, and may also laterally extend from elsewhere along the length of the cartridge 75. As shown, the outer periphery of the flange 75d of the cartridge 75 defines a largest outer perimeter of the cartridge 75. In the illustrated embodiment, the shape of the cartridge 75 is defined by a series of generally cylindrical portions, e.g., a cylindrical neck, body, and flange, and the flange 75d of the cartridge 75 defines a largest outer circumference of the cartridge 75 (but the disclosure is not so limited).

Figure 10:
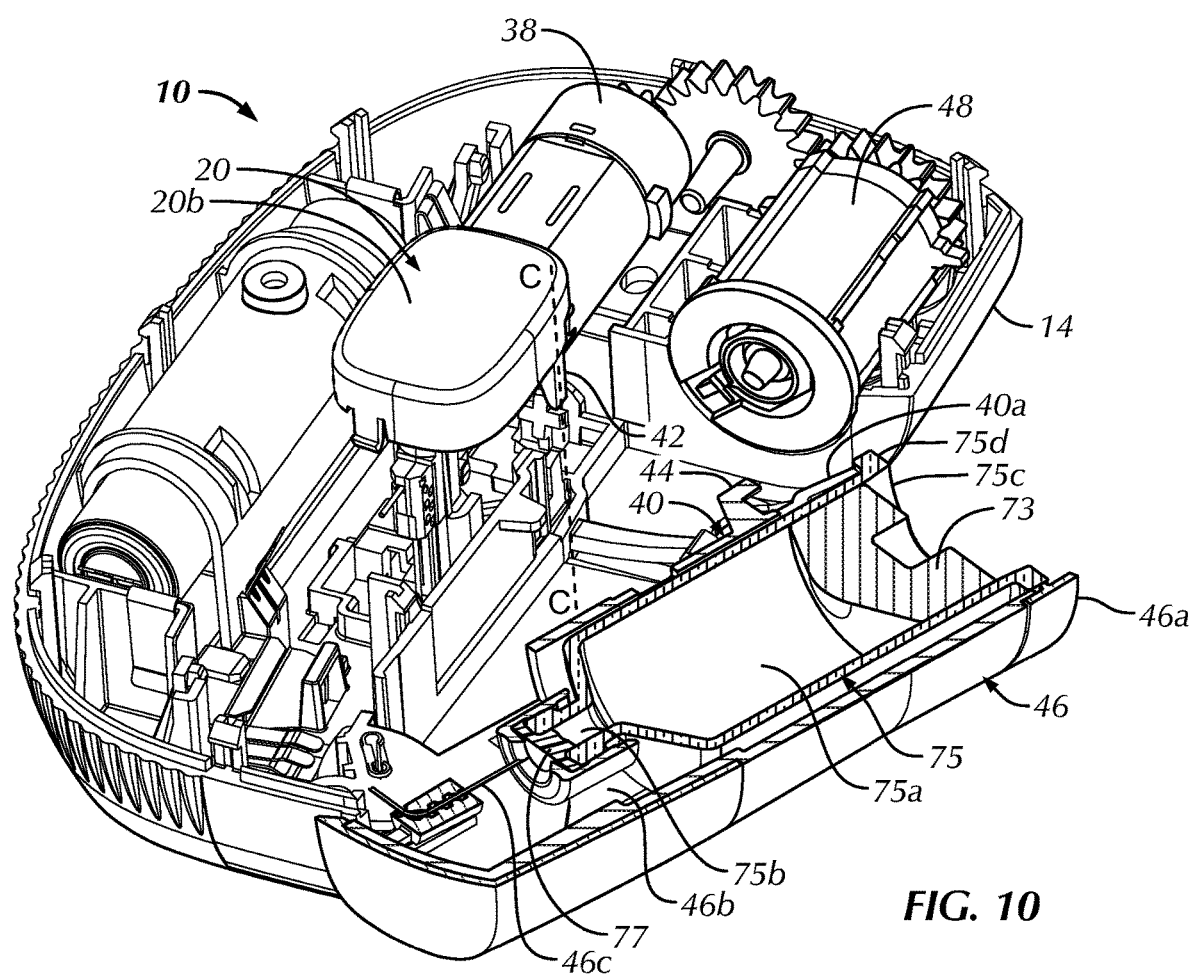
FIG. 10 is a top, front and left side perspective view of the injector of FIG. 1 having a top cover of the injector removed, with an activation button assembly in an unactuated position thereof, a cartridge door in an open position thereof and a sealed cartridge inserted therein.

The cartridge door 46 is movably mounted to the injector housing 12, between an open position (e.g., FIG. 10) and a closed position (FIGS. 1 and 11-13). In the closed position, the interior channel 46b is inaccessible from outside of the injector housing 12. For example, in the illustrated embodiment, the open end 46a of the cartridge door 46 is sufficiently covered by a portion of the injector housing 12 such that access to the interior channel 46b is prevented. In the open position, the open end 46a of the cartridge door 46 is at least partially uncovered, and the interior channel 46b is at least partially accessible from the open end 46a. In a fully open position of the cartridge door 46, as shown in FIG. 10, the open end 46a of the cartridge door 46 is sufficiently uncovered to permit insertion of the cartridge 75 therethrough and into the interior channel 46b.

In the illustrated embodiment, the cartridge door 46 is pivotably attached to the injector housing 12, e.g., via pin connection 50, proximate a closed, distal end of the interior channel 46b, opposite the open end 46a, but the disclosure is not so limited. As shown in FIG. 10, the cartridge door 46 is pivoted away from the injector housing 12 in the open position, whereby the interior channel 46b is accessible from the open end 46a of the cartridge door 46. Other non-limiting examples of a cartridge door 46 movably mounted to an injector housing 12 are described in U.S. Patent Application Publication No. 2018/0154081, entitled, "Cartridge Insertion For Drug Delivery Device," the entire contents of which are incorporated by reference herein.

The cartridge door 46 further includes a cartridge piercing needle 46c mounted within the interior channel 46b. As shown schematically in FIG. 9, the cartridge piercing needle 46c is connected to, and in fluid communication with, the injection needle 18 in a manner well understood by those of ordinary skill in the art, e.g., via a flexible tube (not shown) extending from the piercing needle 46c to the injection needle 18. In the illustrated embodiment, the cartridge piercing needle 46c is positioned proximate the closed, distal end of the interior channel 46b, opposite the open end 46a. The cartridge piercing needle 46c extends inwardly into the interior channel 46b and terminates at a tip of the needle 46c, positioned to face and align with the pierceable septum 77 of the cartridge 75 when the cartridge 75 is inserted into the cartridge door 46. The cartridge piercing needle 46c is configured to fully penetrate the pierceable septum 77 of the cartridge 75 to connect the substance within the cartridge 75 in fluid communication with the injection needle 18 when the injector 10 is activated, as will be described in further detail below.

The injector 10 further includes a driving assembly 48 (see FIGS. 10, 11, and 13 and schematically in FIG. 9) positioned and configured to engage the piston 73 (through the open end 46a of the cartridge door 46 and the second opening 75c of the cartridge 75) subsequent to device activation to expel the substance out of the cartridge 75, as will be described in further detail below. In one non-limiting example, the driving assembly 48 may take the form of a telescopic driving assembly, i.e., a plurality of threaded shafts threadably connected to one another in a telescopic manner whereby rotation of at least one of the shafts linearly translates at least another of the shafts, but the disclosure is not so limited. One example of a telescoping driving assembly is described in U.S. Patent Application Publication No. 2016/0346478, now U.S. Pat. No. 10,149,943, entitled "Linear Rotation Stabilizer For A Telescoping Syringe Stopper Driverdriving Assembly", the entire contents of which are incorporated by reference herein. Another example of a telescoping driving assembly is described in International Application Publication No. WO 2018/222521 A1, entitled "Modular Drive Train For Wearable Injector", the entire contents of which are incorporated by reference herein.

The driving assembly 48 is operatively engaged with the activation button assembly 20. In one non-limiting example, and as shown schematically in FIG. 9, the injector 10 may include a sensor 52, e.g., an optical position sensor, configured to detect movement of the injection needle 18 (in a manner well understood by those of ordinary skill in the art) from the retracted position thereof into the injection position thereof, which is generated (as previously described) by movement of the activation button assembly 20 from the unactuated position thereof to the actuated position thereof. Alternatively, or additionally, the sensor 52 may be configured to detect movement of the activation button assembly 20 itself from the unactuated position thereof to the actuated position thereof. The sensor 52 may be connected to a control assembly 36, e.g., a processor, and configured to transmit an output signal thereto (in a manner well understood by those of ordinary skill in the art) indicative of the injection needle 18 becoming positioned in the injection position thereof. In response, the control assembly 36 may be configured to activate an actuator 38 (in a manner well understood by those of ordinary skill in the art). Non-limiting examples of an actuator 38 include a motor, a spring actuator, a gaseous actuator, a chemical actuator, an electrical actuator, an electromechanical actuator, combinations thereof, or the like. Upon activation, the actuator 38 is configured to drive the driving assembly 48 (in a manner well understood by those of ordinary skill in the art), e.g., via a series of interconnected rotatable gears, from an initial position, unengaged with the piston 73, into engagement with the piston 73.

The injector 10 further includes a deflectable interference member 40 having a resting position (FIGS. 10, 11) in which the interference member 40 limits an insertion depth of the cartridge 75 into the interior channel 46b of the cartridge door 46. When in the resting position thereof, the interference member 40 permits insertion of the cartridge 75 into the interior channel 46b of the door 46 to a sealed position wherein the cartridge 75 is loaded, but remains sealed. That is, the interference member 40 prevents the cartridge 75 from reaching a position wherein the piercing needle 46c fully penetrates the pierceable septum 77, thereby connecting the substance within the cartridge 75 in fluid communication with the injection needle 18. In the illustrated embodiment, the cartridge piercing needle 46c does not engage the septum 77 in the sealed position of the cartridge 75. Alternatively, the cartridge piercing needle 46c may partially penetrate the septum 77 in the sealed position of the cartridge 75, without fully penetrating through the septum 77. As shown best in FIG. 10, the interior channel 46b of the cartridge door 46 defines a length greater than a length of the cartridge 75. Accordingly, in the resting position of the interference member 40, the cartridge 75 is sufficiently insertable into the interior channel 46b of the cartridge door 46 to permit movement of the cartridge door 46 into the closed position thereof, while remaining in the sealed state thereof (FIGS. 10 and 11).

In the illustrated embodiment, the deflectable interference member 40 takes the form of a cantilevered arm/finger defining a deflectable portion of the sidewall of the cartridge door 46. That is, the cantilevered arm 40 is integrally formed with the sidewall of the cartridge door 46, e.g., co-molded therewith, having a first end connected to the cartridge door 46 and extending (as a deflectable portion of the sidewall) to a second, free end 40a proximate the open end 46a of the cartridge door 46. The disclosure is not so limited, however, and the cantilevered arm 40 may be formed separately or individually and connected or attached, directly or indirectly to the cartridge door 46. Alternatively, the deflectable interference member 40 may take other forms capable of performing the function of the interference member 40 disclosed herein, such as, for example, without limitation, a spring actuated deflectable interference member. The cartridge door 46 and the deflectable interference member 40 may each be constructed, for example, from a polymeric or metal material, combinations thereof, or the like.

Figure 11:
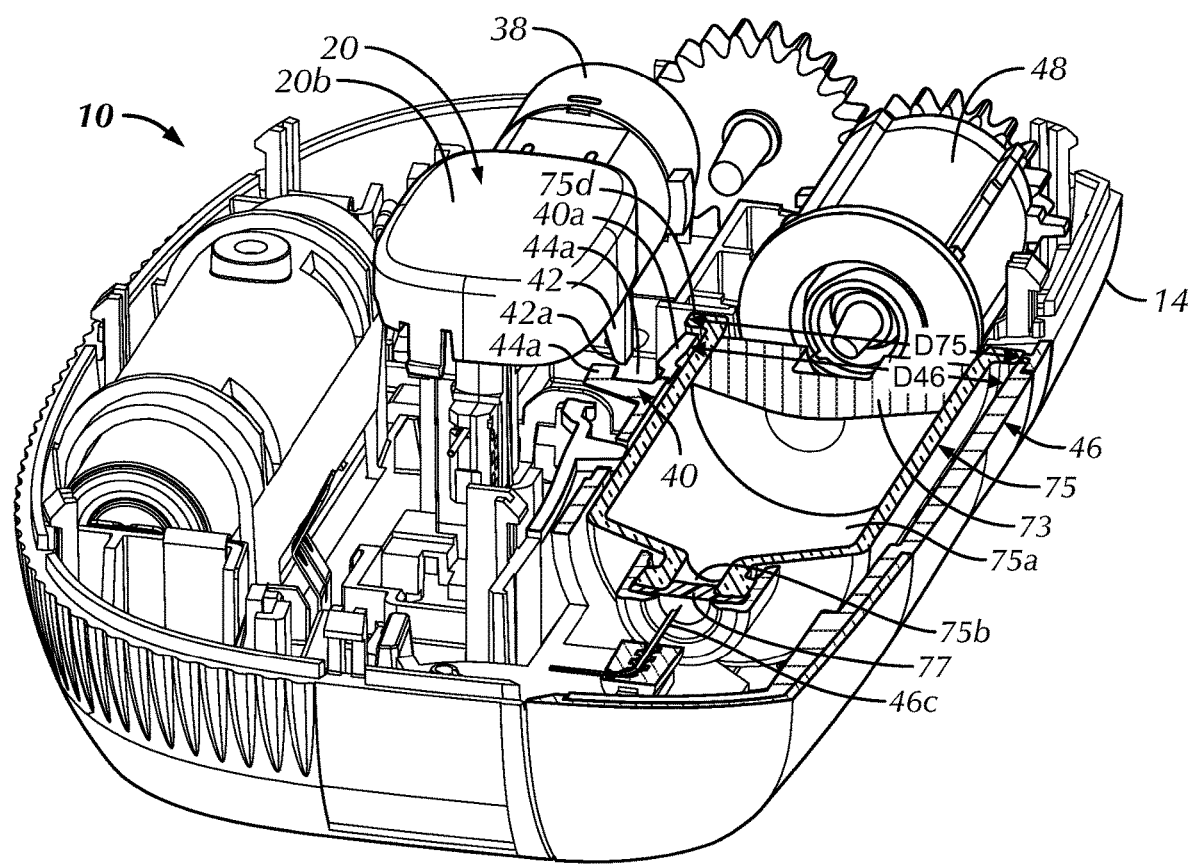
FIG. 11 is a top, front and left side perspective view of the injector of FIG. 1 having the top cover of the injector removed, with the activation button assembly in the unactuated position thereof, the cartridge door in a closed position thereof and the sealed cartridge inserted therein.
Figure 12:
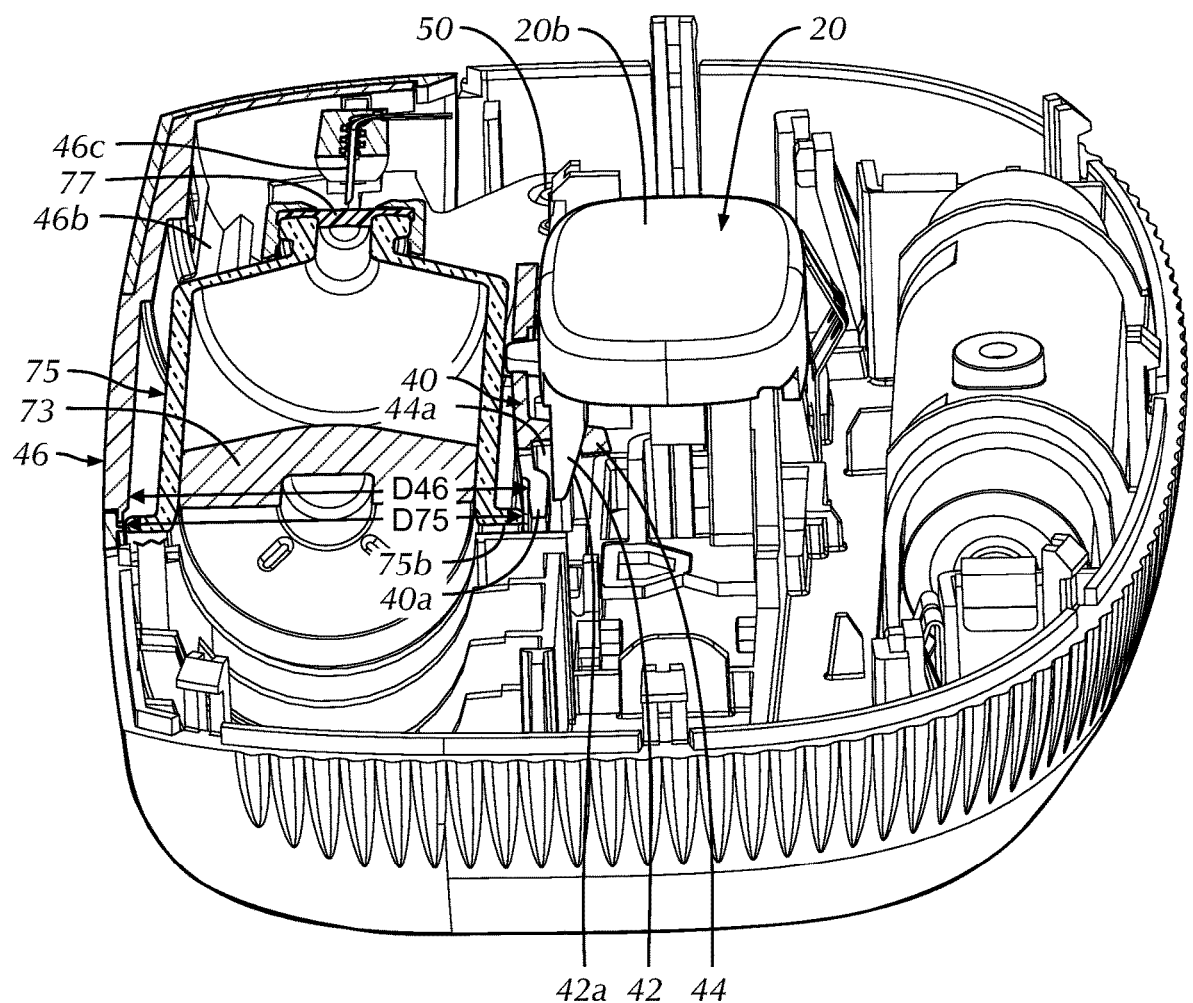
FIG. 12 is a top and right side perspective view of the injector of FIG. 1 having the top cover, a driving assembly and an actuator of the injector removed, with the cartridge door in the closed position thereof and the activation button assembly in an actuated position thereof, thereby deflecting an interference element limiting the insertion depth of the cartridge into the cartridge door.

As shown in FIGS. 11 and 12, an internal diameter D46 of the cartridge door 46 at the second, free end 40*a* of the cantilevered arm 40 is smaller than an outer diameter D75 of the cartridge 75 at the rear flange 75*d* thereof, when the cantilevered arm 40 is in the resting position thereof. As previously described, the rear flange 75*d* defines a largest outer circumference of the cartridge 75. Accordingly, the inner perimeter of the cartridge door 46 at the second, free end 40*a* of the cantilevered arm 40 is smaller than an outer perimeter of the cartridge 75 at the rear flange 75*d* thereof in the resting position of the cantilevered arm 40. When the cartridge door 46 is opened to insert a cartridge therein, the cantilevered arm 40 is positioned in the resting position thereof. Thus, the second, free end 40*a* of the cantilevered arm 40 engages the rear flange 75*d* of the cartridge 75 during insertion of the cartridge 75 into the interior channel 46*b* of the cartridge door 46 and blocks further advancement of the cartridge 75 into the interior channel 46*b*. The cartridge door 46 and the piercing needle 46*c* are sized and dimensioned such that the piercing needle 46*c* does not fully penetrate the septum 77 of the cartridge 75 at the position of the cartridge 75 within the interior channel 46*b* when stopped by the second, free end 40*a* of the cantilevered arm 40.

As shown best in FIGS. 10-13, the activation button assembly 20 includes a post 42 extending therefrom. In the illustrated embodiment, the post 42 extends downwardly (i.e., parallel with button axis B) from the top surface 20*b* of the activation button assembly 20, but the disclosure is not so limited. As shown best in FIGS. 11 and 12, the post 42 tapers to a terminal end thereof opposite from the top surface 20*b*. The post 42 starts to taper at least partially along the length thereof. That is, the post 42 defines a tapered face 42*a* along at least a portion of the length of the post 42, resulting in a gradual thinning of the post 42 in a direction toward the terminal end (otherwise viewed as a gradual thickening of the post 42 from the terminal end thereof in a direction toward the top surface 20*b*). As should be understood, the post 42 may taper along the entire length thereof or along a portion of the length thereof. The post 42 defines a post pathway C (parallel to the button axis B) along which the post 42 travels during movement of the activation button assembly 20 from the unactuated position to the actuated position.

The cantilevered arm 40 defines a hook-shaped tab 44 laterally extending from the sidewall of the cartridge door 46 toward the post pathway C. In the closed position of the cartridge door 46, the hook-shaped tab 44 laterally extends through (into and beyond) the post pathway C (FIG. 11). Accordingly, movement of the activation button assembly 20 from the unactuated position to the actuated position thereof, in the closed position of the cartridge door 46, engages the post 42 with the hook-shaped tab 44. The post 42 slides through a central aperture 44*a* of the hook-shaped tab 44 with the tapered face 42*a* of the post 42 facing toward the hooked end of the tab 44 and away from the cartridge door 46. As the tapered post 42 travels downwardly through the central aperture 44*a* of the tab 44, the increasing thickness of the post 42 (due to the reverse taper) engages and laterally translates the hooked end of the tab 44 (FIG. 12). The tapered face 42*a* of the post 42 is inclined from the terminal end thereof toward the top surface 20*b* in a direction away from the cartridge door 46. Accordingly, the hooked end of the tab 44 is laterally translated away from the cartridge door 46, and, in turn, deflects the cantilevered arm 40 away from the resting position thereof in a direction away from the cartridge door 46. As should be understood, the post 42 may be constructed to define a greater bending stiffness, i.e., resistance against bending deformation/deflection, than the cantilevered arm 40, such that engagement of the post 42 with the hook-shaped tab 44 results in deflection of the cantilevered arm 40. Such properties may be achieved via relative material properties, between the post 42 and the cantilevered arm 40, as well as relative dimensions between the post 42 and the cantilevered arm 40, or a combination thereof.

As shown in FIG. 12, the internal diameter D46 of the cartridge door 46 at the second, free end 40*a* of the cantilevered arm 40 is greater than the outer diameter D75 of the cartridge 75 at the rear flange 75*d* thereof, in the deflected position of the cantilevered arm 40. That is, the inner perimeter of the cartridge door 46 at the second, free end 40*a* of the cantilevered arm 40 is greater than an outer perimeter of the cartridge 75 at the rear flange 75*d* in the deflected position of the cantilevered arm 40. As shown in FIG. 12, the second, free end of the cantilevered arm 40 clears the rear flange 75*d* of the cartridge 75. Thus, when the activation button 22 is depressed from the unactuated position to the actuated position thereof (with the cartridge door 46 in the closed position), deflecting the cantilevered arm 40 with the post 42, the cartridge 75 is unblocked and further advancement of the cartridge 75 into the interior channel 46*b* of the cartridge door 46 is enabled.

Figure 13:
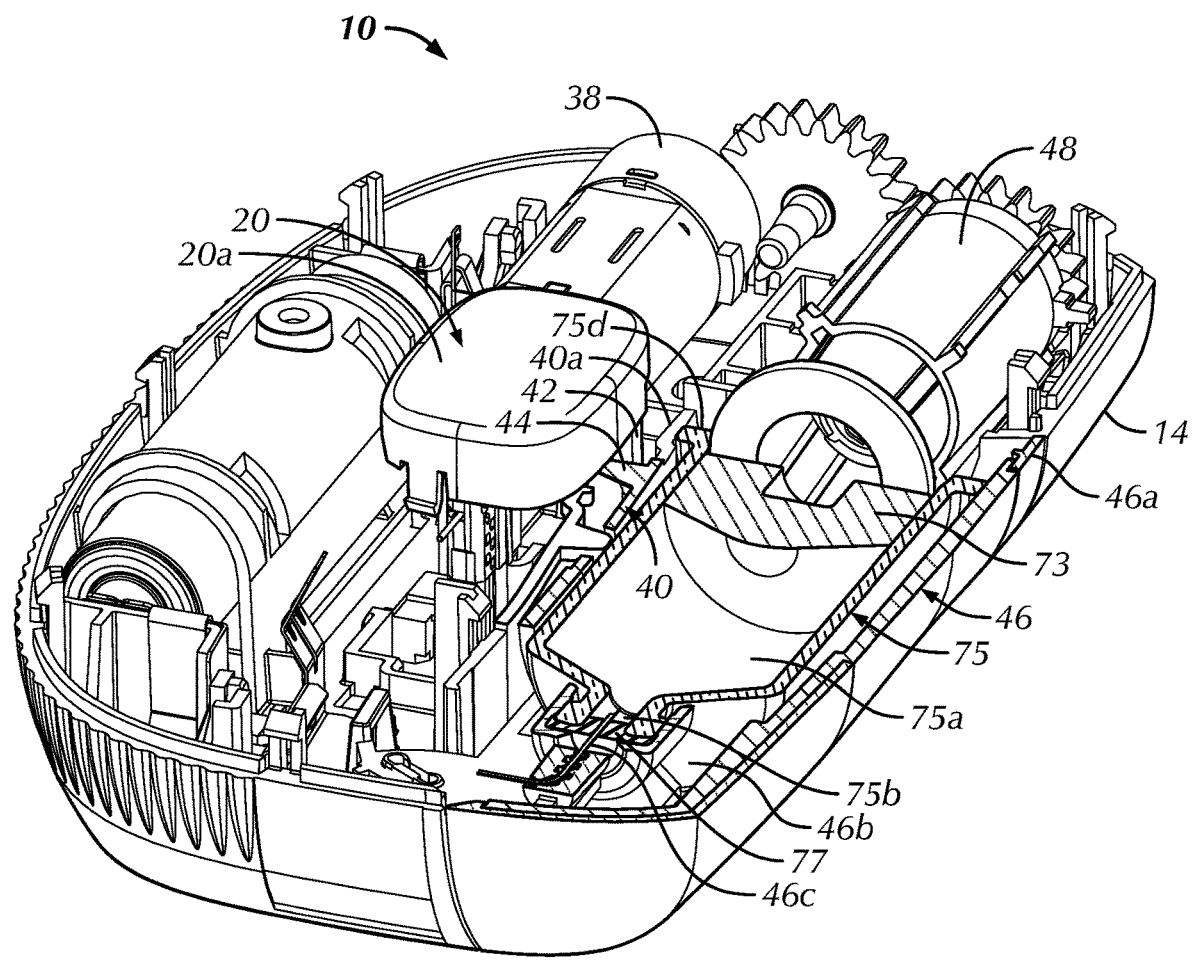
FIG. 13 is a top, front and left side perspective view of the injector of FIG. 1 having the top cover of the injector removed, with the cartridge door in the closed position thereof and the activation button assembly in the actuated position thereof, with the driving assembly advancing the cartridge further into the cartridge door into an unsealed position thereof.

In use, a patient or clinician may initiate operation of the injector 10 by opening the cartridge door 46 and inserting the cartridge 75 into the interior channel 46*b* thereof, until the rear flange 75*d* of the cartridge 75 engages the second, free end 40*a* of the cantilevered arm 40 in the resting position of the cantilevered arm 40 (FIG. 10). Advantageously, the cartridge 75 remains sealed. The cartridge door 46 is thereafter moved, e.g., by the patient or clinician, into the closed position thereof, aligning the cartridge door 46 (and the cartridge 75 therein) with the driving assembly 48 secured within the injector housing 12. When ready for use, the activation button assembly 20 is translated (e.g., by the patient or clinician upon placement of the injector 10 at the injection site on the skin surface of the patient) from the unactuated position thereof to the actuation position, deflecting the cantilevered arm 40 away from the resting position thereof as previously described and freeing the cartridge 75 for further advancement into the interior channel 46*b* of the cartridge door 46. As also previously described, the activation button assembly 20 is operatively connected with the driving assembly 48, and movement of the activation button assembly 20 into the actuated position thereof also drives the driving assembly forward and into engagement with the piston 73 (FIG. 13). Upon initial contact between the driving assembly 48 and the piston 73, the cartridge 75 remains sealed. Thus the driving force of the driving assembly 48 onto the piston 73 drives the entire cartridge 75 forward, whereby the septum 77 is fully penetrated by the piercing needle 46*c* and the cartridge 75 is unsealed. After unsealing of the cartridge 75, the continued driving force of the driving assembly 48 advances the piston 73 forward through the reservoir 75*a* of the cartridge 75 to drive the substance therein through the piercing needle 46*c* and to the injection needle 18 for dispensing of the substance therefrom.

In one embodiment, the cartridge 75 is driven forward until the cartridge 75 reaches a stop surface (not shown). For example, the stop surface may take the form of a step (not shown) laterally inwardly projecting from the inner sidewall of the cartridge door 46 and configured, e.g., positioned and dimensioned, to abut the rear flange 75*d* of the cartridge 75 upon full penetration of the septum 77 by the piercing needle 46*c*. The substance within the cartridge 75 therefore becomes connected in fluid communication with the injection needle 18 upon penetration of the septum 77 and further forward advancement of the cartridge 75 is stopped. Once the cartridge 75 is unsealed and stopped, further driving force of the driving assembly 48 applied to the piston 73 advances the piston forward through the reservoir 75*a* of the cartridge 75 and causes the substance within the reservoir 75*a* to flow through the piercing needle 46*c*, to the injection needle 18, and, to be dispensed out of the injection needle 18.

Advantageously, the cartridge 75 is preserved in a sealed state until the injector 10 is activated for use, as the interference element 40 blocks full insertion of the cartridge 75 until the activation button 22 is translated into the actuated position thereof. Accordingly, the injector 10 is not subjected to leakage, contamination or blockage of flow prior to injector activation. Moreover, if the injector 10 is damaged or the injection is otherwise not performed, e.g., an error occurs and is recognized between initial cartridge 75 loading and actuation of the activation button assembly 20, the cartridge 75 remains sealed and usable with another injector 10.

Figure 14:
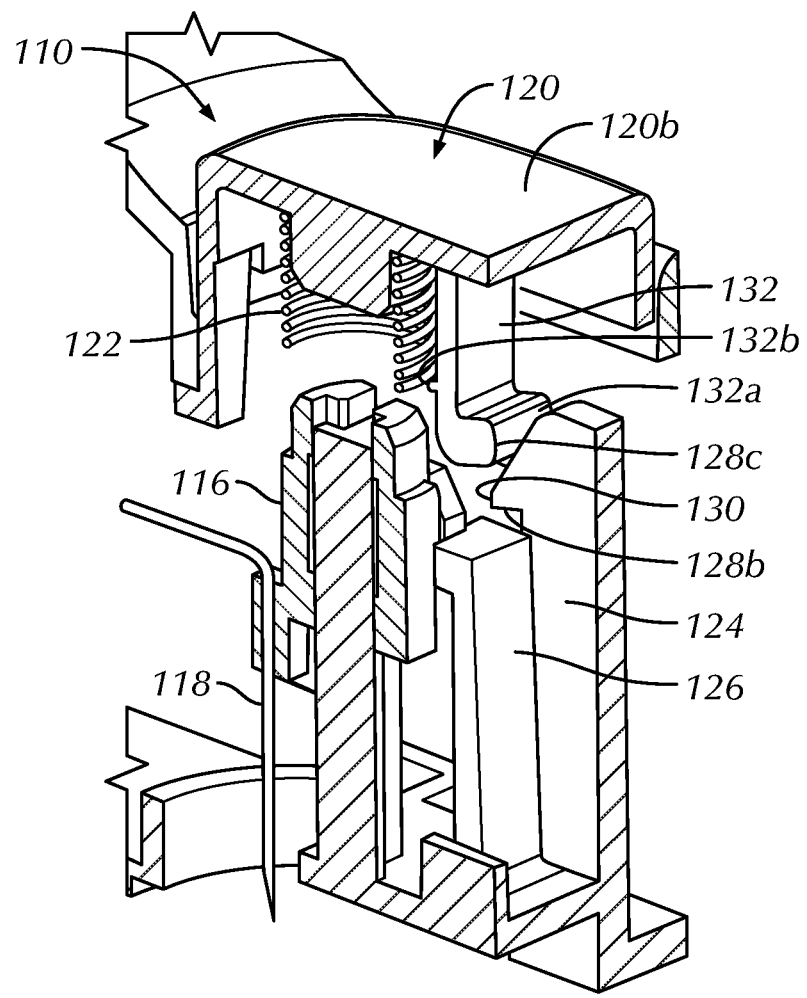
FIG. 14 is an enlarged, partial cross-sectional view of the activation button assembly and the injection needle insertion mechanism in accordance with a second embodiment of the present disclosure, taken along the sectional line 5-5 of FIG. 2, with the activation button assembly in the unactuated position thereof and the injection needle in the retracted position thereof.
Figure 15:
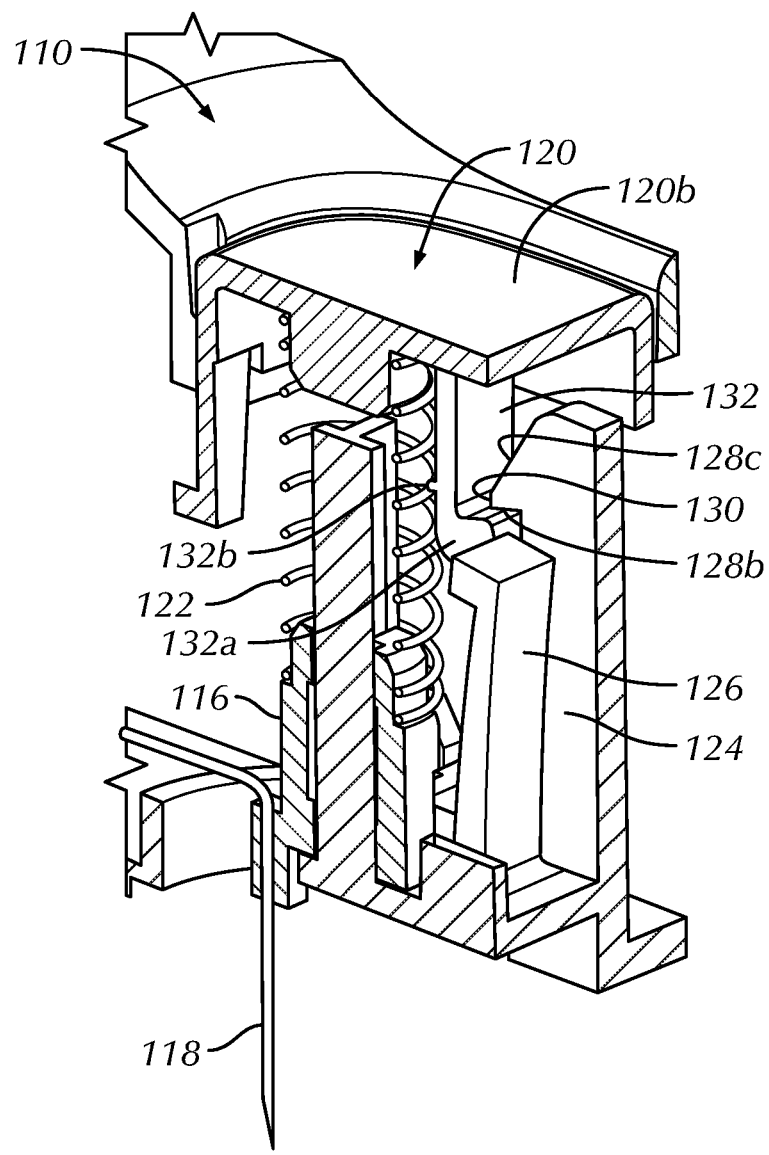
FIG. 15 is an enlarged, partial cross-sectional view of the activation button assembly and the injection needle insertion mechanism of FIG. 14, taken along the sectional line 5-5 of FIG. 2, with the activation button assembly in the actuated position thereof and the injection needle in the injection position thereof.

FIGS. 14-15 illustrate a second embodiment of the injector 110. The reference numerals of the second embodiment are distinguishable from those of the above-described first embodiment (FIGS. 1-13) by a factor of one-hundred (100), but otherwise indicate the same elements as indicated above, except as otherwise specified. The injector 110 of the present embodiment is substantially similar to that of the earlier embodiment. Therefore, the description of certain similarities and modes of operation between the embodiments may be omitted herein for the sake of brevity and convenience, and, therefore, is not limiting.

One difference of the injector 110 over the embodiment shown in FIGS. 1-13, pertains to the configuration of the activation button assembly 120 and the assembly of the biasing member 122. As shown in FIG. 14, the biasing member, e.g., spring, 122 is mounted within the activation button assembly 120 in the stored energy state thereof, when the activation button assembly is in the unactuated position. The first arm 132 of the activation button assembly 120 includes a lip 132*b* laterally extending therefrom in a direction opposite the direction of the flange 132*a*. The spring 122 abuts the underside of the top surface 120*b* of the activation button assembly 120 at one end and engages the lip 132*b* at the opposing end when the actuation button assembly is in the unactuated position thereof.

The flange 132*a* interacts with the elongate first post 124 in a similar manner as described with respect to the embodiment of FIGS. 1-13. In the unactuated position of the activation button assembly 120 (FIG. 14), the lip 132*b* catches the spring 122 and maintains the spring 122 in the energy storing state. The flange 132*a* is engaged with the inclined surface 128*c* of the first post 124, slightly deflecting the first arm 132 laterally in the direction of the lip 132*b*. Depressing the activation button assembly 120 slides the flange 132*a* down the inclined surface 128*c* of the post 124, further deflecting the first arm 132 laterally in the direction of the lip 132*b*, i.e., toward the spring 122. Such deflection of the first arm 132 maintains the engagement of the spring 122 with the lip 132*b*. Such deflection of the first arm 132 (by depressing the activation button assembly 120) also stores potential energy in the first arm 132 to straighten back out, thereby sliding back up the inclined surface 128*c* of the first post 124 and returning the activation button assembly 120 to the unactuated position thereof if the first arm 132 does not travel past the vertex 130, i.e., the threshold point/position.

Movement of the activation button assembly 120 sufficiently such that the flange 132*a* of the first arm 132 surpasses the vertex 130, triggers retraction of the deflected first arm 132 back toward a substantially undeflected state thereof, hooking/snapping the flanged terminal end 132*a* thereof into engagement with the undercut 128*b* of the first post 124 and securing the activation button assembly 120 in the actuated position thereof (FIG. 15). Retraction of the deflected first arm 132 back toward a substantially undeflected state thereof, upon movement of the flange 132*a* beyond the vertex 130, also engages the flange 132*a* with the second post 126 and deflects the second post 126 to release the needle hub 116. Return of the first arm 132 into a substantially undeflected configuration thereof also releases the lip 132*b* from the spring 122. As shown in FIG. 15, the spring 122 is released into the energy releasing state to engage and drive the released needle hub 116 and the injection needle 118 from the retracted position thereof to the injection position thereof.

The reservoir 75*a* can contain a substance, e.g., medicament, comprising an antibody to be dispensed from the injector 10 through the injection needle 18. The medicament, e.g., antibody, is preferably suitable for treatment of a complement associated condition including, but not limited to rheumatoid arthritis, antiphospholipid antibody syndrome, lupus nephritis, ischemia-reperfusion injury, atypical hemolytic uremic syndrome, typical hemolytic uremic syndrome, paroxysmal nocturnal hemoglobinuria, dense deposit disease, neuromyelitis optica, multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, myasthenia gravis, cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection (e.g., kidney transplant), Hashimoto's thyroiditis, type I diabetes, psoriasis, pemphigus, autoimmune hemolytic anemia, idiopathic thrombocytopenic purpura, Goodpasture's syndrome, Degos disease, and catastrophic antiphospholipid syndrome, preferably atypical hemolytic uremic syndrome (aHUS) and/or paroxysmal nocturnal hemoglobinuria (PNH).

Preferred antibodies for treatment of a complement associated condition include anti-C5 antibodies or antigen binding fragments thereof. As used herein, an "anti-C5 antibody" refers to a monoclonal antibody or antigen binding fragment thereof, preferably a humanized IgG monoclonal antibody, that binds to complement component C5 (e.g., human C5) and inhibits cleavage of C5 into fragments C5a and C5b. Anti-C5 antibodies, among other functions, inhibit terminal complement (e.g., the assembly and/or activity of the C5b-9

TCC) and C5a anaphylatoxin-mediated inflammation, and can thus be used to treat complement associated conditions. Preferably, an anti-C5 antibody, or antigen binding fragment thereof, comprises heavy chain complementarity determining regions (CDRs) HCDR1, HCDR2, and HCDR3 of SEQ ID NOs: 1, 2, and 3, respectively; and light chain CDRs LCDR1, LCDR2, and LCDR3 of SEQ ID NOs: 4, 5, and 6, respectively. In one embodiment, the anti-C5 antibody, or antigen binding fragment thereof, comprises a heavy chain variable region (VH) and a light chain variable region (VL) having the amino acid sequences of SEQ ID NOs: 7 and 8, respectively. Preferably, the anti-C5 antibody comprises a heavy chain having the amino acid sequence of SEQ ID NO: 9 and a light chain having the amino acid sequence of SEQ ID NO: 10.

In preferred embodiments, an anti-C5 antibody, or antigen binding fragment thereof, is an IgG antibody comprising one or more amino acid substitutions in the Fc constant region that increase the binding affinity of the antibody for Fc receptors, such as the neonatal Fc receptor (FcRn), thus reducing the rate of elimination of the antibody from circulation and/or increasing the half-life of the antibody. For example, the CH3 domain of the Fc constant region can comprise Met-429-Leu and Asn-435-Ser substitutions at residues corresponding to methionine 428 and asparagine 434 of a native human IgG Fc constant region according to EU numbering. In some embodiments, an anti-C5 antibody comprises HCDR1, HCDR2, and HCDR3 of SEQ ID NOs: 1, 2, and 3, respectively; light chain CDRs LCDR1, LCDR2, and LCDR3 of SEQ ID NOs: 4, 5, and 6, respectively; and a heavy chain constant region having the amino acid sequence of SEQ ID NO: 11.

In a particular embodiment, the anti-C5 antibody is ravulizumab (also known as ALXN1210). Ravulizumab is described in U.S. Pat. No. 9,079,949 (referred to as BNJ441), which is herein incorporated by reference in its entirety. Anti-C5 antibodies, or antigen binding fragments thereof, e.g., ravulizumab, can be prepared by any method known in the art in view of the present disclosure for preparing monoclonal antibodies including, but not limited to, hybridoma production.

The substance, e.g., medicament, contained in reservoir 75a can be a pharmaceutical composition comprising an anti-C5 antibody, or antigen binding fragment thereof. The pharmaceutical composition is preferably formulated for subcutaneous administration. Examples of formulations suitable for subcutaneous administration include, but are not limited to, solutions, suspensions, emulsions, and dry (e.g., lyophilized) products that can be dissolved or suspended in a pharmaceutically acceptable carrier for injection. A "carrier" refers to any excipient, diluent, buffer, stabilizer, or other material known in the art for pharmaceutical formulations. Pharmaceutically acceptable carriers in particular are non-toxic and should not interfere with the efficacy of the active ingredient. The pharmaceutically acceptable carriers include excipients and/or additives suitable for use in the pharmaceutical compositions known in the art, e.g., as listed in "Remington: The Science & Practice of Pharmacy," 19$^{th}$ ed., Williams & Williams (1995), and in the "Physician's Desk Reference," 52$^{nd}$ ed., Medical Economics, Montvale, N.J. (1998). Examples of pharmaceutically acceptable carriers suitable for use in compositions formulated for subcutaneous administration include water, saline, dextrose, glycerol, ethanol, etc.

In some embodiments, an anti-C5 antibody, or antigen binding fragment thereof, such as ravulizumab, can be co-formulated or co-administered with a substance to optimize subcutaneous delivery of the anti-C5 antibody, or antigen binding fragment thereof, e.g., by extending the dosing interval. For example, an anti-C5 antibody can be co-formulated with a hyaluronidase enzyme, such as recombinant human hyaluronidase (rHuPH20). Hyaluronidase enzymes, such as rHuPH20 can be soluble. For example, human hyaluronidase which is normally membrane anchored via a GPI anchor, can be made soluble by truncation of and removal of all or a portion of the GPI anchor at the C-terminus. In certain embodiments, the rHuPH20 is ENHANZE®, manufactured by Halozyme. Hyaluronidase is an enzyme that degrades hyaluronic acid (EC 3.2.1.35) and lowers the viscosity of hyaluron in the extracellular matrix, thereby increasing tissue permeability and facilitating subcutaneous administration of therapeutic agents, such as antibodies. Co-formulation or co-administration of an antibody with recombinant human hyaluronidase, such as rHuPH20, may allow for increased injection volumes, increased bioavailability from subcutaneous injection, and/or reduced administration frequency (e.g., from once weekly administration or administration once every two weeks to once monthly administration). The bioavailability of a therapeutic agent (e.g., antibody) administered in combination with hyaluronidase can be greater than 90% of the bioavailability of the therapeutic agent following intravenous administration. Thus, when administered subcutaneously in the present of a hyaluronidase enzyme such as rHuPH20, the therapeutic agent (e.g., antibody) can be administered at a lower frequency at the same dose used for intravenous administration for the particular indication. In a particular embodiment, a substance, e.g., medicament, contained in reservoir 75a comprises recombinant human hyaluronidase and an anti-C5 antibody, or antigen binding fragment thereof, comprising HCDR1, HCDR2, and HCDR3 of SEQ ID NOs: 1, 2, and 3, respectively; and light chain CDRs LCDR1, LCDR2, and LCDR3 of SEQ ID NOs: 4, 5, and 6, respectively. Preferably, the anti-C5 antibody, or antigen binding fragment thereof, further comprises a heavy chain constant region having the amino acid sequence of SEQ ID NO: 11, and more preferably comprises a heavy chain having the amino acid sequence of SEQ ID NO: 9 and a light chain having the amino acid sequence of SEQ ID NO: 10.

In some embodiments, an anti-C5 antibody, or antigen binding fragment thereof, is co-formulated with a recombinant human hyaluronidase in a composition for subcutaneous administration at a dosage frequency of about once per month. Such formulations can be administered subcutaneously at dosages equivalent to dosages provided by intravenous administration. Typically, hyaluronidase, e.g., recombinant human hyaluronidase, is administered subcutaneously at about 500 units, 1000 units, 2000 units, 5000 units, 10000 units, 30000 units 40000 units, 50000 units or 100000 units of more, wherein a unit is defined as the amount of enzyme that liberates one micromole of N-acetyl-glucosamine from hyaluronic acid per minute at 37° C. and pH 4.0 as measured by a standard United States Pharmacopeia (USP) assay. One of ordinary skill in the art can readily measure the activity of hyaluronidase based on general knowledge in the art in view of the present disclosure. Generally, dosages of an antibody are about 50 mg/kg body weight (BW) to 2 g/kg BW, e.g., 50 mg/kg BW, 100 mg/kg BW, 200 mg/kg BW, 300 mg/kg BW, 400 mg/kg BW, 500 mg/kg BW, 600 mg/kg BW, 700 mg/kg BW, 800 mg/kg BW, 900 mg/kg BW, 1 g/kg BW, or 2 g/kg BW and dosages of hyaluronidase are about 10 units/gram to 500 units per gram or more of antibody.

For example, when co-formulated or co-administered with an anti-C5 antibody or antigen binding fragment thereof, hyaluronidase (e.g., rHuPH20) can be administered at 10 units/gram to 500 units/gram or more of the anti-C5 antibody, or antigen binding fragment thereof. Preferably, the anti-C5 antibody or antigen-binding fragment thereof is co-formulated in a pharmaceutical composition with hyaluronidase (e.g., rHuPH20) to achieve dosages for which current intravenous preparations are prepared and administered for treatment of a complement associated condition, such as atypical hemolytic uremic syndrome (aHUS) and/or paroxysmal nocturnal hemoglobinuria (PNH). Exemplary dosages for treatment of aHUS and/or PNH with an anti-C5 antibody or antigen binding fragment thereof include about 1000 mg to 3600 mg of an anti-C5 antibody or antigen binding fragment thereof per administration, such as 1000, 2000, 2200, 2400, 2600, 2800, 3000, 3200, 3400, or 3600 mg per administration, such as about 50 mg/kg BW to 100 mg/kg BW. Hyaluronidase (e.g., rHuPH20) can be included in the formulation in an amount such that the dosage of hyaluronidase is about 10 units per gram to about 500 units per gram or more of the anti-C5 antibody or antigen binding fragment thereof. However, lower and higher dosages are also contemplated by the invention as determined by the person administering or person supervising administration in order to achieve the desired result.

Also provided is a method of treating a subject in need of treatment of a complement associated condition comprising administering an anti-C5 antibody, or antigen binding fragment thereof, to the subject using a device as described herein. The subject can be any mammal, preferably a human, in need of treatment of a complement associated condition, preferably aHUS and/or PNH. PNH and aHUS are both rare disorders driven by chronic uncontrolled complement activation resulting in inflammation and cellular damage.

In particular, PNH is an acquired hemolytic disorder that occurs most frequently in adults in which uncontrolled complement activity leads to systemic complications, principally through intravascular hemolysis and platelet activation. The disease begins with the clonal expansion of a hematopoietic stem cell that has acquired a somatic mutation in the PIGA gene. Consequently, PNH blood cells lack the glycophosphatidylinositol (GPI) anchor protein and are deficient in the membrane-bound complement inhibitory proteins CD55 and CD59. In the absence of CD55, there is increased deposition of complement protein C3 cleavage products on blood cell membrane surfaces, in turn leading to cleavage of C5 into C5a and C5b. The pathology and clinical presentations in patients with PNH are driven by uncontrolled terminal complement activation. C5a is a potent anaphylatoxin, chemotactic factor, and cell-activating molecule that mediates multiple pro-inflammatory and pro-thrombotic activities. C5b recruits the terminal complement components C6, C7, C8, and C9 to form the proinflammatory, pro-thrombotic cytolytic pore molecule C5b-9, a process that under normal circumstances would be blocked on the red blood cell (RBC) membrane by CD59. In patients with PNH, however, these final steps proceed unchecked, culminating in hemolysis and the release of free hemoglobin, as well as platelet activation. The signs and symptoms of PNH can be attributed to chronic, uncontrolled complement C5 cleavage, and release of C5a and C5b-9 leading to RBC hemolysis, which together result in release of intracellular free hemoglobin and lactate dehydrogenase (LDH) into circulation as a direct consequence of hemolysis; irreversible binding to and inactivation of nitric oxide (NO) by hemoglobin, and inhibition of NO synthesis; vasoconstriction and tissue-bed ischemia due to absence of vasodilatory NO, as well as possible microthrombi manifesting as abdominal pain, dysphagia, and erectile dysfunction; platelet activation; and/or a pro-inflammatory and prothrombotic state.

Similar to PNH, the pathology and clinical presentations of patients with aHUS are also driven by terminal complement activation. More specifically, activation of C5 and dysregulation of complement activation lead to endothelial damage, platelet consumption, and thrombotic microangiopathic (TMA) events, characterized by thrombocytopenia, mechanical intravascular hemolysis, and kidney injury. Importantly, approximately 20% of patients experience extra-renal manifestations of disease as well, including central nervous system, cardiac, gastrointestinal, distal extremities, and severe systemic organ involvement. Symptoms of aHUS are well-known to those of skill in the art of rare disease or kidney disease medicine and include, e.g., severe hypertension, proteinuria, uremia, lethargy/fatigue, irritability, thrombocytopenia, microangiopathic hemolytic anemia, and renal function impairment (e.g., acute renal failure). aHUS can be genetic, acquired, or idiopathic. aHUS can be considered genetic when two or more (e.g., three, four, five, or six or more) members of the same family are affected by the disease at least six months apart and exposure to a common triggering agent has been excluded, or when one or more aHUS-associated gene mutations (e.g., one or more mutations in CFH, MCP/CD46, CFB, or CFI) are identified in a subject. For example, a subject can have CFH-associated aHUS, CFB-associated aHUS, CFI-associated aHUS, or MCP-associated aHUS. Up to 30% of genetic aHUS is associated with mutations in CFH, 12% with mutations in MCP, 5-10% with mutations in CFI, and less than 2% with mutations in CFB. Genetic aHUS can be multiplex (i.e., familial; two or more affected family members) or simplex (i.e., a single occurrence in a family). aHUS can be considered acquired when an underlying environmental factor (e.g., a drug, systemic disease, or viral or bacterial agents that do not result in Shiga-like exotoxins) or trigger can be identified. aHUS can be considered idiopathic when no trigger (genetic or environmental) is evident.

Administration of an anti-C5 antibody, or antigen binding fragment thereof, using a device as described herein is via the subcutaneous route. A device as described herein can be used to deliver an effective amount of an anti-C5 antibody, or antigen binding fragment thereof, e.g., ravulizumab, to a predetermined tissue site with the subject. The anti-C5 antibody, or antigen binding fragment thereof, is preferably comprised in a pharmaceutical composition suitable for subcutaneous administration, optionally co-formulated with a recombinant human hyaluronidase enzyme, that is held within reservoir 75a, and is dispensed from injector 10 through the injection needle 18 resulting in subcutaneous administration to the subject. An "effective amount" amount as used herein with respect to an anti-C5 antibody, or antigen binding fragment thereof, refers to an amount of the anti-C5 antibody, or antigen binding fragment thereof that provides the desired biological, therapeutic, and/or prophylactic result. That result can be a(n) reduction, amelioration, palliation, lessening, delaying, and/or alleviation of one or more of the signs, symptoms, or causes of a disease (e.g., PNH or aHUS), or any other desired alteration of a biological system. In one illustrative example, an "effective amount" is the amount of anti-C5 antibody, or antigen binding fragment thereof, that alleviates at least one symptom of PNH (e.g., fatigue, abdominal pain, dyspnea, dysphagia, chest pain, or erectile dysfunction) or at least one symptom of aHUS (e.g., severe hypertension, proteinuria, uremia, lethargy/fatigue, irritability, thrombocytopenia, microangiopathic hemolytic anemia, and renal function impairment (e.g., acute renal failure)). An effective amount can be administered in one or more administrations.

The frequency of administration of an anti-C5 antibody, or antigen binding fragment thereof, using a device as described herein for treatment of a complement associated condition can vary depending on a variety of factors such as the condition to be treated, the subject to be treated (e.g., age, health), etc. For example, for treatment of PNH and/or aHUS, an anti-C5 antibody, or antigen binding fragment thereof, e.g., ravulizumab, can be administered once per week, such as once per week for 1 week, 2 weeks, 3 weeks, 4 weeks, 2 months, 3, months, 4 months, 5 months, 6 months, 7 months, or 8 months or more. In those embodiments in which an anti-C5 antibody, e.g., ravulizumab is co-formulated or co-administered with a recombinant human hyaluronidase enzyme (e.g., ENHANZE®), the dosing interval for treatment of PNH and/or aHUS can be extended to once every two weeks or once per month for 1 month, 2 months, 3 months, 4 months, 5 months, 6 month, 7 months, or 8 months or more.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as set forth in the appended claims.

SEQUENCE LISTING

| SEQ ID NO: | Description | Sequence |
|---|---|---|
| 1 | HCDR1 | GHIFSNYWIQ |
| 2 | HCDR2 | EILPGSGHTE YTENFKD |
| 3 | HCDR3 | YFFGSSPNWY FDV |
| 4 | LCDR1 | GASENIYGAL N |
| 5 | LCDR2 | GATNLAD |
| 6 | LCDR3 | QNVLNTPLT |
| 7 | VH | QVQLVQSGAE VKKPGASVKV SCKASGHIFS NYWIQWVRQA PGQGLEWMGE ILPGSGHTEY TENFKDRVTM TRDTSTSTVY MELSSLRSED TAVYYCARYF FGSSPNWYFD VWGQGTLVTV SS |
| 8 | VL | DIQMTQSPSS LSASVGDRVT ITCGASENIY GALNWYQQKP GKAPKLLIYG ATNLADGVPS RFSGSGSGTD FTLTISSLQP EDFATYYCQN VLNTPLTFGQ GTKVEIK |
| 9 | Heavy chain | QVQLVQSGAE VKKPGASVKV SCKASGHIFS NYWIQWVRQA PGQGLEWMGE ILPGSGHTEY TENFKDRVTM TRDTSTSTVY MELSSLRSED TAVYYCARYF FGSSPNWYFD VWGQGTLVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVLH EALHSHYTQK SLSLSLGK |
| 10 | Light chain | DIQMTQSPSS LSASVGDRVT ITCGASENIY GALNWYQQKP GKAPKLLIYG ATNLADGVPS RFSGSGSGTD FTLTISSLQP EDFATYYCQN VLNTPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 11 | Heavy chain constant region | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP APPVAGPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVLHEA LHSHYTQKSL SLSLGK |

We claim:

1. An injector comprising:
   an injector housing;
   an injection needle translatable between a retracted position, at which at least a tip of the injection needle is contained within the injector housing, and an injection position, at which at least the tip of the injection needle protrudes from the injector housing;
   an activation button assembly movably mounted to the injector housing and operatively connected to the injection needle, the activation button assembly being translatable from an unactuated position to an actuated position to drive the injection needle from the retracted position to the injection position;
   a cartridge door movably mounted to the injector housing between an open position and a closed position, the cartridge door comprising:
      an open end,
      an interior channel having a cartridge mounted therein, the cartridge containing an antibody to be dispensed and having an opening at a front end of the cartridge sealed by a pierceable septum and a flange at a rear end thereof, and
      a cartridge piercing needle mounted within the interior channel and connected in fluid communication with the injection needle, the cartridge piercing needle being configured to fully penetrate the pierceable septum of the cartridge to connect the antibody within the cartridge in fluid communication with the injection needle; and
   a deflectable interference member engaging the rear end flange of the cartridge in a resting position of the interference member, thereby limiting an insertion depth of the cartridge into the interior channel of the cartridge door to a sealed position, at which the cartridge piercing needle does not fully penetrate the pierceable septum,
   wherein:
      the cartridge door is movable to the closed position in the sealed position of the cartridge, and movement of the activation button assembly from the unactuated position to the actuated position, in the closed position of the cartridge door, deflects the interference member out of engagement with the rear end flange of the cartridge, thereby enabling further advancement of the cartridge into the interior channel of the cartridge door to an unsealed position, at which the cartridge piercing needle fully penetrates the pierceable septum.

2. The injector of claim 1, further comprising a driving assembly engageable with the cartridge to expel the antibody therefrom, the driving assembly being operatively engaged with the activation button assembly and being configured to drive the cartridge from the sealed position to the unsealed position upon movement of the activation button assembly from the unactuated position to the actuated position.

3. The injector of claim 1, wherein the deflectable interference member comprises a cantilevered arm.

4. The injector of claim 3, wherein the cantilevered arm defines a first end connected to the cartridge door and extending to a second, free end proximate the open end of the cartridge door.

5. The injector of claim 4, wherein the cartridge door comprises a sidewall and the cantilevered arm defines a deflectable portion of the sidewall of the cartridge door.

6. The injector of claim 5, wherein the sidewall of the cartridge door defines a first internal perimeter at the second, free end of the cantilevered arm when the cantilevered arm is in the resting position, and the sidewall of the cartridge door defines a second internal perimeter at the second, free end of the cantilevered arm when the cantilevered arm is deflected from the resting position, the first internal perimeter being smaller than a largest outer perimeter of the cartridge insertable into the interior channel, thereby limiting the insertion depth of the cartridge into the interior channel of the cartridge door, and the second internal perimeter being greater than the largest outer perimeter of the cartridge, thereby enabling further advancement of the cartridge into the interior channel of the cartridge door.

7. The injector of claim 3, wherein the activation button assembly comprises a post extending therefrom to a terminal end having a tapered face, the post having a post pathway along which the post travels from the unactuated position of the activation button assembly to the actuated position of the activation button assembly, and wherein the cantilevered arm comprises a tab laterally extending therefrom toward the post pathway, the tab having a hooked end facing the tapered face of the post, wherein movement of the activation button assembly from the unactuated position to the actuated position, in the closed position of the cartridge door, engages the post with the tab, the tapered face engaging and laterally translating the hooked end, and, in turn, deflecting the cantilevered arm away from the resting position.

8. The injector of claim 1, further comprising a biasing member connected with the activation button assembly and the injection needle, the biasing member being stabilized in a stored energy state in the unactuated position of the activation button assembly, and released in the actuated position of the activation button assembly into an energy releasing state to drive the injection needle from the retracted position to the injection position, wherein:
a position of the activation button assembly between the unactuated position and the actuated position defines a threshold point, and
movement of the activation button assembly beyond the threshold point secures the activation button assembly in the actuated position and the injection needle in the injection position.

9. The injector of claim 8, wherein the biasing member biases the activation button assembly into the unactuated position and returns the activation button assembly to the unactuated position in response to movement of the activation button assembly not surpassing the threshold point.

10. The injector of claim 9, further comprising a needle hub movably mounted within the injector housing, the injection needle being supported by the needle hub, and the needle hub and the injection needle being translatable between the retracted position and the injection position.

11. The injector of claim 10, further comprising:
an elongate first post connected with the injector housing and projecting upwardly therefrom, the elongate first post having an upper end comprising a downwardly inclined surface and an undercut underlying the inclined surface; and
a deflectable second post connected with the injector housing and projecting upwardly therefrom, the deflectable second post including a flange supporting a portion of the needle hub thereon, thereby securing the needle hub and the injection needle in the retracted position, wherein:
the activation button assembly comprises a downwardly projecting first arm having a flanged terminal end slidable along the inclined surface of the elongate first post, the first arm being elastically deflectable from an original state thereof,
movement of the activation button assembly slides the flanged terminal end of the first arm along the inclined surface of the first post, thereby elastically deflecting the first arm away from the original state,
the inclined surface and the undercut of the elongate first post meet at a vertex defining the threshold point,
movement of the activation button assembly beyond the vertex triggers retraction of the first arm back toward the original state, thereby hooking the flanged terminal end onto the undercut of the elongate first post and securing the activation button assembly in the actuated position, and
movement of the activation button assembly beyond the vertex also engages the flanged terminal end of the first arm with the second post and deflects the second post, whereby the deflected second post releases the needle hub, and, in turn, releases the biasing member into the energy releasing state to drive the needle hub and the injection needle from the retracted position to the injection position.

12. A method of dispensing an antibody from an injector, the injector having an injector housing, an injection needle movable from a retracted position, at which at least a tip of the injection needle is contained within the injector housing, and an injection position, at which at least the tip of the injection needle protrudes from the injector housing, an activation button assembly movably mounted to the injector housing and operatively connected to the injection needle, a cartridge door movably mounted to the injector housing between an open position and a closed position, the cartridge door having an open end, an interior channel, and a cartridge piercing needle mounted within the interior channel and connected in fluid communication with the injection needle, and a driving assembly operatively engaged with the activation button assembly, the method comprising:

inserting a cartridge into the interior channel of the cartridge door in the open position of the cartridge door, the cartridge containing the antibody in a sealed reservoir thereof and having an opening at a front end of the reservoir sealed by a pierceable septum and a flange at a rear end of the reservoir;

engaging the rear end flange of the cartridge with a deflectable interference member of the injector in a resting position of the interference member, thereby limiting an insertion depth of the cartridge into the interior channel of the cartridge door to a sealed position, at which the cartridge piercing needle does not fully penetrate the pierceable septum;

moving the cartridge door into the closed position; and moving the activation button assembly from an unactuated position to an actuated position thereby:

deflecting the interference member out of engagement with the rear end flange of the cartridge, activating the driving assembly to advance the rear end flange of the cartridge past the interference member and drive the cartridge from the sealed position to an unsealed position, at which the cartridge piercing needle fully penetrates the pierceable septum of the cartridge and connects the antibody within the cartridge in fluid communication with the injection needle, and driving the injection needle from the retracted position to the injection position and dispensing the antibody therefrom.

13. The method of claim 12, wherein the driving of the injection needle to the injection position comprises protruding at least the tip of the injection needle from the injector housing, and dispensing the antibody from the injection needle.

14. The method of claim 12, wherein the injector further includes a sensor connected to a control assembly, the method further comprising:

detecting, via the sensor, at least one of (i) movement of the activation button assembly from the unactuated position thereof to the actuated position or (ii) movement of the injection needle from the retracted position thereof into the injection position; and activating the driving assembly, via the control assembly, upon said detecting.

15. The method of claim 12, wherein the activation button assembly includes a post extending therefrom to a terminal end having a tapered face, the post having a post pathway along which the post travels from the unactuated position of the activation button assembly to the actuated position of the activation button assembly, and wherein the interference member includes a cantilevered arm defining a deflectable portion of a sidewall of the cartridge door, whereby a first end of the cantilevered arm is connected to the sidewall and extends to a second, free end proximate the open end of the cartridge door, the cantilevered arm including a tab laterally extending therefrom toward the post pathway, the tab having a hooked end facing the tapered face of the post, and wherein moving of the activation button assembly from the unactuated position to the actuated position comprises engaging the tapered face of the post with the hooked end of the tab, laterally translating the hooked end, and, in turn, deflecting the cantilevered arm out of engagement with the rear end flange of the cartridge.

16. An injector comprising:

an injector housing;

an injection needle translatable between a retracted position, at which at least a tip of the injection needle is contained within the injector housing, and an injection position, at which at least the tip of the injection needle protrudes from the injector housing;

a cartridge door movably mounted to the injector housing between an open position and a closed position, the cartridge door comprising:

an open end, an interior channel having a cartridge mounted therein, the cartridge containing an antibody to be dispensed and having an opening at a front end of the cartridge sealed by a pierceable septum and a flange at a rear end thereof, and a cartridge piercing needle mounted within the interior channel and connected in fluid communication with the injection needle, the cartridge piercing needle being configured to fully penetrate the pierceable septum of the cartridge to connect the antibody within the cartridge in fluid communication with the injection needle; and a deflectable interference member engaging the rear end flange of the cartridge in a resting position of the interference member, thereby limiting an insertion depth of the cartridge into the interior channel of the cartridge door to a sealed position, at which the cartridge piercing needle does not fully penetrate the pierceable septum.

17. The injector of claim 16, further comprising an activation button assembly movably mounted to the injector housing and operatively connected to the injection needle, the activation button assembly being translatable from an unactuated position to an actuated position to drive the injection needle from the retracted position to the injection position.

18. The injector of claim 17, further comprising a driving assembly engageable with the cartridge to expel the antibody therefrom, the driving assembly being operatively engaged with the activation button assembly and being configured to drive the cartridge upon movement of the activation button assembly from the unactuated position to the actuated position.

19. The injector of claim 17, wherein the deflectable interference member comprises a cantilevered arm defining a first end connected to the cartridge door and extending to a second, free end proximate the open end of the cartridge door.

20. The injector of claim 19, wherein the cartridge door comprises a sidewall and the cantilevered arm defines a deflectable portion of the sidewall of the cartridge door.

21. The injector of claim 20, wherein the sidewall of the cartridge door defines a first internal perimeter at the second, free end of the cantilevered arm when the cantilevered arm is in the resting position, and the sidewall of the cartridge door defines a second internal perimeter at the second, free end of the cantilevered arm when the cantilevered arm is deflected from the resting position, the first internal perimeter being smaller than a largest outer perimeter of the cartridge insertable into the interior channel, thereby limiting the insertion depth of the cartridge into the interior channel of the cartridge door, and the second internal perimeter being greater than the largest outer perimeter of the cartridge, thereby enabling further advancement of the cartridge into the interior channel of the cartridge door.

22. The injector of claim 19, wherein the activation button assembly comprises a post extending therefrom to a terminal end having a tapered face, the post having a post pathway along which the post travels from the unactuated position of the activation button assembly to the actuated position of the activation button assembly, and wherein the cantilevered arm comprises a tab laterally extending therefrom toward the post pathway, the tab having a hooked end facing the tapered face of the post, wherein movement of the activation button assembly from the unactuated position to the actuated position, in the closed position of the cartridge door, engages the post with the tab, the tapered face engaging and laterally translating the hooked end, and, in turn, deflecting the cantilevered arm away from the resting position.

23. The injector of claim 17, further comprising a biasing member connected with the activation button assembly and the injection needle, the biasing member being stabilized in a stored energy state in the unactuated position of the activation button assembly, and released in the actuated position of the activation button assembly into an energy releasing state to drive the injection needle from the retracted position to the injection position, wherein:
   a position of the activation button assembly between the unactuated position and the actuated position defines a threshold point, and
   movement of the activation button assembly beyond the threshold point secures the activation button assembly in the actuated position and the injection needle in the injection position.

24. The injector of claim 23, wherein the biasing member biases the activation button assembly into the unactuated position and returns the activation button assembly to the unactuated position in response to movement of the activation button assembly not surpassing the threshold point.

25. The injector of claim 24, further comprising a needle hub movably mounted within the injector housing, the injection needle being supported by the needle hub, and the needle hub and the injection needle being translatable between the retracted position and the injection position.

26. The injector of claim 25, further comprising:
   an elongate first post connected with the injector housing and projecting upwardly therefrom, the elongate first post having an upper end comprising a downwardly inclined surface and an undercut underlying the inclined surface; and
   a deflectable second post connected with the injector housing and projecting upwardly therefrom, the deflectable second post including a flange supporting a portion of the needle hub thereon, thereby securing the needle hub and the injection needle in the retracted position, wherein:
   the activation button assembly comprises a downwardly projecting first arm having a flanged terminal end slidable along the inclined surface of the elongate first post, the first arm being elastically deflectable from an original state thereof,
   movement of the activation button assembly slides the flanged terminal end of the first arm along the inclined surface of the first post, thereby elastically deflecting the first arm away from the original state,
   the inclined surface and the undercut of the elongate first post meet at a vertex defining the threshold point,
   movement of the activation button assembly beyond the vertex triggers retraction of the first arm back toward the original state, thereby hooking the flanged terminal end onto the undercut of the elongate first post and securing the activation button assembly in the actuated position, and
   movement of the activation button assembly beyond the vertex also engages the flanged terminal end of the first arm with the second post and deflects the second post, whereby the deflected second post releases the needle hub, and, in turn releases the biasing member into the energy releasing state to drive the needle hub and the injection needle from the retracted position to the injection position.

\* \* \* \* \*

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: HCDR1

<400> SEQUENCE: 1

Gly His Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Glu Ile Leu Pro Gly Ser Gly His Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<223> OTHER INFORMATION: HCDR3

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: LCDR1

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3
```

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<223> OTHER INFORMATION: VH

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 9
<211> LENGTH: 448
<212> TYPE: PRT
<213> ORGANISM: Artificial Sequence
<220> FEATURE:
<223> OTHER INFORMATION: heavy chain -continued

```
<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

Arg Trp Gln Glu Gly Asn Val Phe Ser Cys Ser Val Leu His Glu Ala
                420                 425                 430

Leu His Ser His Tyr Thr Gln Lys Ser Leu Ser Leu Ser Leu Gly Lys
                435                 440                 445

<210> SEQ ID NO 10
<211> LENGTH: 214
<212> TYPE: PRT
<213> ORGANISM: Artificial Sequence
<220> FEATURE:
<223> OTHER INFORMATION: light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 326
<212> TYPE: PRT
<213> ORGANISM: Artificial Sequence
<220> FEATURE:
<223> OTHER INFORMATION: heavy chain constant region

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

-continued

```
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
             85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
             165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
            290                 295                 300

Ser Val Leu His Glu Ala Leu His Ser His Tyr Thr Gln Lys Ser Leu
305                 310                 315                 320

Ser Leu Ser Leu Gly Lys
            325
```